United States Patent
Faça et al.

(10) Patent No.: US 10,738,127 B2
(45) Date of Patent: Aug. 11, 2020

(54) MONOCLONAL ANTIBODIES PREVENT CELL SURFACE PROTEIN SHEDDING AND BLOCK TUMOR GROWTH

(71) Applicant: VERITAS BIOTECNOLOGIA LTDA, Ribeirão Preto (BR)

(72) Inventors: Sandra Rodrigues Pereira Faça, Ribeirão Preto (BR); Vitor Marcel Faça, Ribeirão Preto (BR)

(73) Assignee: Veritas Biotecnologia LTDA, Ribeirão Preto, SP (BR)

( * ) Notice: Subject to any disclaimer, the term of this patent is extended or adjusted under 35 U.S.C. 154(b) by 0 days.

(21) Appl. No.: 16/308,443

(22) PCT Filed: Jun. 12, 2017

(86) PCT No.: PCT/IB2017/053475
§ 371 (c)(1),
(2) Date: Dec. 7, 2018

(87) PCT Pub. No.: WO2017/212462
PCT Pub. Date: Dec. 14, 2017

(65) Prior Publication Data
US 2019/0256609 A1    Aug. 22, 2019

Related U.S. Application Data

(60) Provisional application No. 62/348,347, filed on Jun. 10, 2016.

(51) Int. Cl.
| | |
|---|---|
| *C07K 16/00* | (2006.01) |
| *A61K 39/395* | (2006.01) |
| *C07K 16/28* | (2006.01) |
| *A61P 35/00* | (2006.01) |
| *C07K 14/28* | (2006.01) |
| *C07K 16/32* | (2006.01) |
| *C12N 5/12* | (2006.01) |
| *G01N 33/574* | (2006.01) |
| *A61K 39/00* | (2006.01) |

(52) U.S. Cl.
CPC ...... *C07K 16/2896* (2013.01); *A61K 39/0011* (2013.01); *A61K 39/001166* (2018.08); *A61P 35/00* (2018.01); *C07K 14/28* (2013.01); *C07K 16/32* (2013.01); *C12N 5/12* (2013.01); *G01N 33/57492* (2013.01); *A61K 2039/507* (2013.01); *C07K 2317/24* (2013.01); *C07K 2317/565* (2013.01); *C07K 2317/73* (2013.01); *C07K 2317/76* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,260,189 A | 11/1993 | Formoso et al. | |
| 5,610,281 A | 3/1997 | Brenner et al. | |
| 2005/0245453 A1 | 11/2005 | Robakis et al. | |
| 2013/0287784 A1 | 10/2013 | Brouxhon et al. | |
| 2015/0004167 A1* | 1/2015 | Wu | C07K 16/2809 424/136.1 |

OTHER PUBLICATIONS

Marambaud et al., A presenilin-1/γ-secretase cleavage releases the E-cadherin intracellular domain and regulates disassembly of adherens junctions. EMBO J. 21(8):1948-1956, 2002 (Year: 2002).*
Biocompare: The Buyer's Guide for life Scientists: Anti-epidermal growth factor receptor antibodiy products. p. 1, Jun. 8, 2020. https://www.biocompare.com/pfu/110447/soids/318519/Antibodies/epidermal_growth_factor_receptor (Year: 2020).*
International Preliminary Report on Patentability for PCT/IB2017/053475 dated Dec. 11, 2018.

* cited by examiner

*Primary Examiner* — Maher M Haddad
(74) *Attorney, Agent, or Firm* — Rodney J. Fuller; Booth Udall Fuller, PLC

(57) ABSTRACT

The present invention provides antibodies that target an E-cadherin linker segment, homologous to other segments adjacent to cell membrane in cancer cell shed proteins for diagnosis and therapy of cancers of epithelial origin. We design this peptide based in experimental observations that demonstrate shedding of E-cadherin and extracellular domains of other cell surface proteins during cancer progression and metastasis and based on our observation that a proline residue after transmembrane domain is present in many proteins on the cell surface that are targets for proteolytic processing. The corresponding antibodies were validated in vitro and in vivo using animal models and have showed no toxicity and significant tumor regression for gastric cancer, including potentiation of commercial drug, when utilized in combination.

17 Claims, 18 Drawing Sheets
Specification includes a Sequence Listing.

| Sequence | Gene | SEQ ID NO: |
|---|---|---|
| KAQPVEAGLQIPAILGILGGILALLILILLLF | CDH1 | 5 |
| PGQEAGLGQVPLIVGILLVLMAVVLASLI | PMEL | 6 |
| TTSGP-IRTPQIPEWLIILASLLALALILA | CD44 | 7 |
| MAASLSPGALIALLVCVLILVLVLLILTLR | MHC-I | 8 |
| PKIPSIATGMVGALLLLLVALGIGLFMRR | EGFR | 9 |
| PPEPSVPLLPLLVAGAVLLVILVLGVMVARR | NOTCH | 10 |
| SSQPTIPIVGIIAGLVLLGAVIT | HLA-I | 11 |
| PMRWPFFLFIPFIIFCVLIAIM | FTNB | 12 |
| VQDSSSVPLPTFLVAGGSLAFGTLLC | ILR6 | 13 |

FIG. 2

```
>sp|P12830|CADH1_HUMAN Cadherin-1 OS=Homo sapiens GN=CDH1 PE=1 SV=3
MGPWSRSLSALLLLLQVSSWLCQEPEPCHPGFDAESYTFTVPRRHLERGRVLGRVNFEDC    60
TGRQRTAYFSLDTRFKVGTDGVITVKRPLRFHNPQIHFLVYAWDSTYRKFSTKVTLNTVG    120
HHRPPPHQASVSGIQAELLTFPNSSPGLRRQKRDWVIPPISCPENEKGPFPKNLVQIKS    180
NKDKEGKVFYSITGQGADTPPVGVFIIERETGWLKVTEPLDRERIATYTLFSHAVSSNGN    240
AVEDPMEILITVTDQNDNKPEFTQEVFKGSVMEGALPGTSVMEVTATDADDVNTYNAAI    300
AYTILSQDPELPDKNMFTINRNTGVISVVTTGLDRESFPTYTLVVQAADLQGEGLSTTAT    360
AVITVTDTNDNPPIFNPTTYKGQVPENEANVVITTLKVTDADAPNTPAWEAVYTILNDDG    420
GQFVVTTNPVNNDGILKTAKGLDFEAKQQYILHVAVTNVVPFEVSLTTSTATVTVDVLDV    480
NEAPIFVPPEKRVEVSEDFGVGQEITSYTAQEPDTMEQKITYRIWRDTANWLEINPDTG    540
AISTRAELDREDEHVNSTYTALIIATDNGSPVATGTGTLLLILSDVNDNAPIPEPRTI    600
FFCERMPKPQVINIIDADLPNTSPETAELTHGASANWTIQYNDPTQESILKPMALEV    660
GDYKINLKLMDNQNKDQVTLEVSVCDCEGAAGVCRKAQPVEAGIQIPAILGILGGILAL    720
LILILLFLRRAVVKEPLLPPEDDTRDNVYYYDEEGGGEEDQDFDLSQLHRGLDARP    780
EVTRNDVAPTLMSVPRYLPRPANPDEIGNFIDENLKAADTDPTAPPYDSLLVFDYEGSGS    840
EAASLSSLNSSESDKDQDYDYLNEWGNRFKKLLADMYGGGEDD                    882
```

FIG. 3

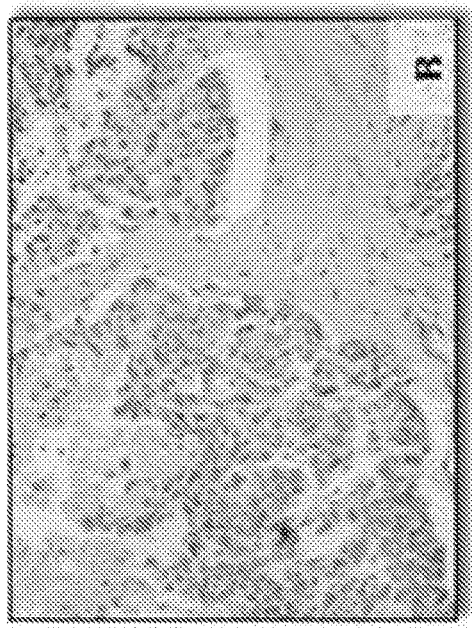
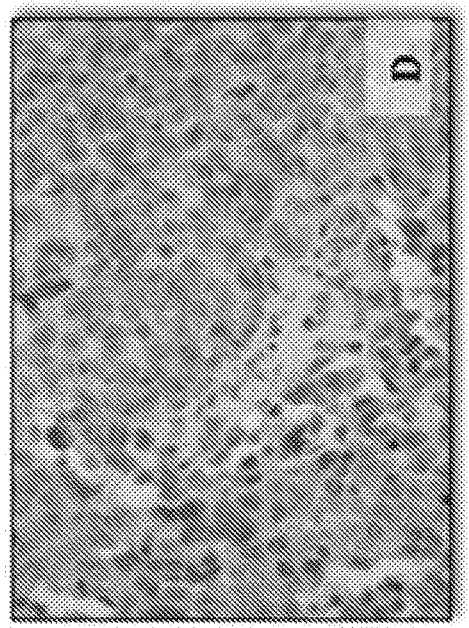
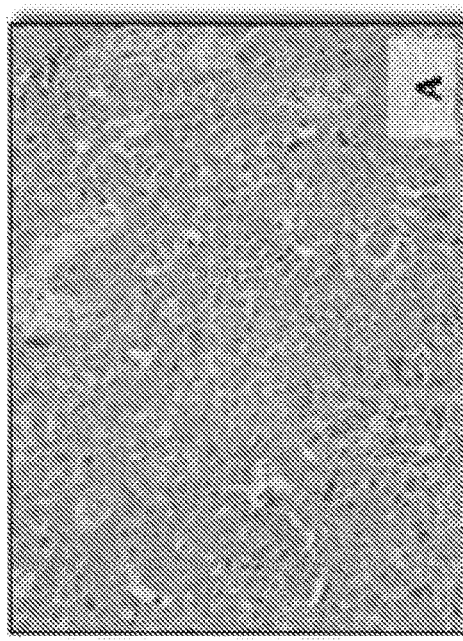
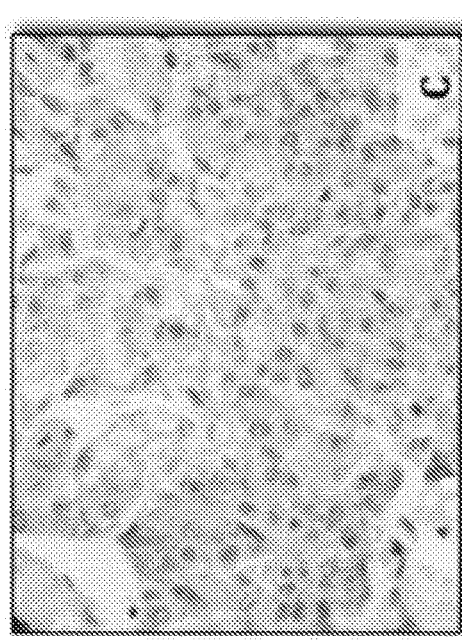
A- Primary lung carcinoma (200x)
B- Primary ovarian carcinoma (200x)
C- Primary ovarian carcinoma (400x)
D- Primary lung carcinoma (400x)
FIG. 13

MONOCLONAL ANTIBODIES PREVENT CELL SURFACE PROTEIN SHEDDING AND BLOCK TUMOR GROWTH

CROSS-REFERENCE TO RELATED APPLICATIONS

The present application is the U.S. National Stage of International Application No. PCT/IB2017/053475, filed Jun. 12, 2017, which claims priority to U.S. Provisional Application No. 62/348,347, filed Jun. 10, 2016, the entire contents and disclosure of which are herein incorporated by reference in their entireties.

FIELD OF THE INVENTION

The present invention relates to the development of therapeutic antibodies to prevent release of cleavage of extracellular domain of transmembrane proteins and to the diagnosis and treatment of cancer. In some aspects, the invention relates to agents for suppressing cell proliferation and/or anticancer agents.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 12 kilobyte ASCII (text) file named "11170.003_Sequence_Listing" created on Jun. 12, 2017.

BACKGROUND OF THE INVENTION

In normal tissues, cells grow and differentiate in a very controlled way. This process is controlled by a number of intracellular and extracellular signaling molecules. However, the well-controlled cellular signaling process may be disrupted by a large variety of processes, for example various genetic mutations. When disruption of cellular proliferation and differentiation pathways occurs, several diseases or proliferative disorders are initiated and generate a tumor, which can develop into cancer. There are several strategies for treating proliferative disorders, which include chemotherapy, radiotherapy, immunotherapy, or a combination of these treatments. However, certain cancers are not responsive or only partially responsive to these treatments. In other cases, such treatment strategies are not available or do not represent a feasible therapy within defined standards of patient care. Even with important improvements in cancer patient care over the years, survival rates for several types of tumors remain low. Accordingly, there is still a great need for the development of new strategies for therapy and diagnostics for proliferative disorders.

In recent years, monoclonal antibodies have been considered the most successful and important strategy for treating cancer patients. Monoclonal antibodies are known to have high target specificity and low incidence of side effects. These antibodies inhibit specific signaling pathways involved in tumor growth as well as induce immunological responses against tumor cells. Examples of antibodies successfully used for cancer treatment include, trastuzumab, which is an antibody for treating solid tumors expressing HER2, and rituximab, which is an antibody that targets CD20 for treating non-Hodgkin lymphoma. Due to cancer heterogeneity, it is highly desirable to develop antibody therapeutic agents against cancers for which there are few therapeutic options and/or against which the currently available therapeutic agents are ineffective (Scott A M et al. *Nature Reviews Cancer* 12, 278-287, 2012). Moreover, the combination of monoclonal antibodies targeting several pathways simultaneously, leads to additive or synergistic effects and represents a current trend in cancer therapy. (Henricks L M et al, *Cancer Treat Rev.* 41, 859-867, 2015).

SUMMARY OF THE INVENTION

The invention relates to novel monoclonal antibodies targeting the linker segment that connects extracellular domains and transmembrane domains in E-cadherin and other homologous proteins.

In some embodiments, the present invention relates to an isolated or purified antibody or subsequence thereof that binds to a region of CDH1 between the extracellular domain and the transmembrane domain, wherein the antibody or subsequence comprises heavy chain and light chain variable region complementarity determining regions (CDRs) sequences identical to heavy chain and light chain variable region sequence CDRs of an antibody produced by hybridoma cell line VLS-C1G (ATCC Accession No. PTA-124082).

In other embodiments, the present invention relates to n isolated or purified antibody or subsequence thereof that binds to an extracellular domain of CDH1, wherein the antibody or subsequence comprises a heavy chain variable region sequence and a light chain variable region sequence identical to a heavy chain variable region sequence and a light chain variable region sequence of an antibody produced by hybridoma cell line VLS-C1G (ATCC Accession No. PTA-124082).

In yet other embodiments, the present invention relates to an isolated or purified anti-E-cadherin antibody or subsequence thereof, wherein the antibody or subsequence binds to an epitope region of E-cadherin comprising the sequence set forth in SEQ ID NO: 1 or comprising the sequence set forth in SEQ ID NO: 2.

In some aspects, the present invention relates to an antibody produced by hybridoma cell line VLS-C1G (ATCC Accession No. PTA-124082) or subsequence thereof.

In other aspects, the antibody or subsequence binds to a sequence of 5-20 amino acids between the region of the extracellular domain and the transmembrane domain of CDH1. In yet other aspects, the antibody or subsequence binds to an amino sequence comprising the sequence set forth in SEQ ID NO:3 or SEQ ID NO:4.

In one embodiment, the antibody the antibody has the ability to inhibit E-cadherin cleavage by matrix metallopeptidase 9 (MMP-9). In another embodiment, the antibody or subsequence thereof is humanized.

In other aspects, the substance of the antibody comprises a single-chain variable fragment (scFv) comprising a heavy chain variable region and light chain variable region of the antibody. In a particular aspect, the scFv is part of a multivalent scFv. In another aspect, the multivalent scFv is a diabody.

In other embodiments, the antibody or subsequence thereof is labeled with one or more labels selected from the group consisting of a biotin label, a fluorescent label, an enzyme label, a coenzyme label, a chemiluminescent label, and a radioactive isotope label.

In certain aspects, the present invention is directed to a pharmaceutical composition comprising: the antibody or subsequence as disclosed herein and a pharmaceutically acceptable excipient or carrier. In one aspect, the composition further comprises an additional antibody subsequence thereof that binds to a member of the epidermal growth factor receptor family. In one aspect, the member of the epidermal growth factor receptor family is HER2. In another aspect, the additional antibody is trastuzumab.

In yet other embodiments, the present invention relates to a hybridoma cell line producing a monoclonal antibody as disclosed herein. In one embodiment, the hybridoma cell line consists of the hybridoma cell line VLS-C1G (ATCC Accession No. PTA-124082).

In other aspects, the present invention relates to a monoclonal antibody targeting the linker segment that connects an extracellular domain and a transmembrane domain in CDH1. In a certain aspect, the linker segment comprises the sequence set forth in SEQ ID NO: 1. In another aspect, antibody is produced using an antigenic peptide comprising the sequence set forth in SEQ ID NO: 3.

In other embodiments, the present invention relates to a pharmaceutical composition for inhibiting the activity of a metalloprotease comprising: a synthetic polypeptide comprising a sequence of 5-20 amino acids between the extracellular domain and the transmembrane domain of a transmembrane protein; and a pharmaceutically acceptable excipient or carrier, wherein the sequence of 5-20 amino acids between the extracellular domain and the transmembrane domain comprises a proline residue among the 15 amino acids preceding the transmembrane domain in the transmembrane protein.

In one aspect, the transmembrane protein is selected from the group consisting of: CDH1, PMEL, CD44, EGFR, NOTCH, HLA-I, FTNB, and ILR6. In another aspect, the metalloprotease is MMP9 and the synthetic polypeptide comprises a sequence selected from the group consisting of: SEQ ID NO: 1 or SEQ ID NO: 2.

In yet other embodiments, the present invention relates to a method of inhibiting tumor growth in a mammal comprising administering an effective amount of the antibody or subsequence thereof as disclosed herein to the mammal.

In other aspects, the present invention relates to a method of treating an adenocarcinoma expressing CDH1 in a mammal comprising administering an effective amount the antibody or subsequence thereof as disclosed herein to the mammal. In one aspect, the tumor or adenocarcinoma is of gastric or ovarian origin. In another aspect, the mammal is a human. In certain aspects, the method further comprises administering a chemotherapeutic agent to the mammal.

In yet other aspects, the present invention relates to a method of diagnosing cancer, the method comprising: obtaining a test tissue sample from a subject at risk of having a cancer and a control tissue sample known to be negative for the cancer; and detecting the expression of CDH1 in the test tissue sample and the control tissue sample with an antibody or subsequence thereof as disclosed herein; wherein the test tissue sample comprises cancer cells where CDH1 expression is reduced compared to the control sample.

In certain aspects, the present invention relates to a method of diagnosing cancer, the method comprising: obtaining a biological sample from a subject at risk of having a cancer and a control sample known to be negative for the cancer; and detecting the expression of soluble E-cadherin (sECAD) in the biological sample and the control sample with an antibody or subsequence thereof as disclosed herein; wherein increased expression of sECAD compared to the control sample indicates the presence of cancer in the subject. In one aspect, the biological sample is selected from the group consisting of blood, serum, plasma, saliva, and urine.

In other embodiments, the present invention relates to a method of inhibiting a metal metalloprotease in a subject, the method comprising administering to the subject an effective amount of the antibody or subsequence as disclosed herein. In one embodiment, the metalloprotease is MMP9.

In yet other embodiments, the present invention relates to a method of inhibiting the shedding of an extracellular domain of a transmembrane protein in a subject, the method comprising administering to the subject an effective amount of the antibody or subsequence thereof as disclosed herein or the pharmaceutical composition as disclosed herein.

In one embodiment, the invention is directed to isolated or purified antibody or subsequence thereof that binds to a region of CDH1 (also known as E-cadherin) between the extracellular domain and the transmembrane domain. For example, the antibody or subsequence binds to a sequence of 5-20 amino acids between the region of the extracellular domain and the transmembrane domain of CDH1. In some aspects, the first 5-10 amino acids of the sequence of 5-20 amino acids between the region of the extracellular domain and the transmembrane domain of CDH1 comprises a proline. In other aspects, the sequence of 5-20 amino acids between the extracellular domain and the transmembrane domain comprises a proline residue among the 15 amino acids preceding the transmembrane domain in the transmembrane protein.

In certain embodiments, the antibody or subsequence thereof binds to VEAGLQIPA (SEQ ID NO: 1) or RKAQPVEAGLQIPA (SEQ ID NO: 2). In one aspect, the antibodies or subsequence thereof are produced by the hybridoma cell line VLS-C1G (ATCC Patent Deposit Designation PTA-124082). In other embodiments, the antibody or subsequence thereof comprises a heavy chain variable region sequence and a light chain variable region sequence identical to a heavy chain variable region sequence and a light chain variable region sequence of an antibody produced by the VLS-C1G cell line. For example, the antibody or subsequence comprises heavy chain and light chain variable region complementarity determining regions (CDRs) sequences identical to heavy chain and light chain variable region sequence CDRs of an antibody produced by the VLS-C1G cell line.

In some implementations, the antibody or subsequence thereof is humanized. In other implementations, the antibody is labeled with one or more labels selected from the group consisting of a biotin label, a fluorescent label, an enzyme label, a coenzyme label, a chemiluminescent label, and a radioactive isotope label.

In some implementations, the substance of the antibody comprises a single-chain variable fragment (scFv), which comprising a heavy chain variable region and light chain variable region of the antibody. In some embodiments, the scFv is part of a multivalent scFv, for example, a diabody.

In another embodiment, the invention is directed to hybridomas that produce the antibodies of the present application. For example, the hybridoma cell line VLS-C1 G. The invention is also directed to a polypeptide which comprises an amino acid sequence which is substantially the same as the amino acid sequence of the variable region of the monoclonal antibody produced by VLS-C1G. In some aspects, the invention is directed a nucleic acid that encodes amino acid sequence which is substantially the same as the amino acid sequence of the variable region of the monoclonal antibody produced by VLS-C1G.

In another embodiment, the invention is directed to pharmaceutical compositions comprising the antibody or subsequence thereof of the invention and a pharmaceutically acceptable excipient or carrier. In still another implementation, the pharmaceutical composition further comprises the antibody or subsequence thereof of the invention and an additional antibody or subsequent thereof that binds to a member of the epidermal growth factor receptor family. For example, the member of the epidermal growth factor receptor family is HER2. As such, the additional antibody of the composition is trastuzumab.

The invention is also directed pharmaceutical composition for inhibiting the activity of a metalloprotease comprising: a synthetic polypeptide comprising a sequence of 5-20 amino acids between the extracellular domain and the transmembrane domain of a transmembrane protein; and a pharmaceutically acceptable excipient or carrier. In certain aspects, the sequence of 5-20 amino acids between the extracellular domain and the transmembrane domain comprises a proline residue among the 15 amino acids preceding the transmembrane domain, among the 14 amino acids preceding the transmembrane domain, among the 13 amino acids preceding the transmembrane domain, among the 12 amino acids preceding the transmembrane domain, among the 11 amino acids preceding the transmembrane domain, among the 10 amino acids preceding the transmembrane domain, among the 9 amino acids preceding the transmembrane domain, among the 8 amino acids preceding the transmembrane domain, among the 7 amino acids preceding the transmembrane domain, among the 6 amino acids preceding the transmembrane domain, among the 5 amino acids preceding the transmembrane domain, among the 4 amino acids preceding the transmembrane domain, among the 3 amino acids preceding the transmembrane domain, or among the 2 amino acids preceding the transmembrane domain in the transmembrane protein. In one aspect, the sequence of 5-20 amino acids between the extracellular domain and the transmembrane domain comprises a proline residue among the 15 amino acids preceding the transmembrane domain in the transmembrane protein. In another aspect, the sequence of 5-20 amino acids between the extracellular domain and the transmembrane domain comprises a proline residue among the 10 amino acids preceding the transmembrane domain in the transmembrane protein.

In some aspects, the synthetic polypeptide comprising a sequence of 5-20 amino acids between the extracellular domain and the transmembrane domain of CDH1, PMEL, CD44, EGFR, NOTCH, HLA-I, FTNB, or ILR6. In some embodiments, the metalloprotease inhibited is MMP9 and the synthetic polypeptide comprises the sequence set forth in SEQ ID NO:3 (VEAGLQIPAC) or SEQ ID NO:4 (RKAQPVEAGLQIPAC).

In another embodiment, the invention is directed to methods of inhibiting tumor growth and/or treating adenocarcinomas expressing CDH1 in a mammal. The methods comprise administering an effective amount of any one of the antibodies or subsequence thereof of the invention to the mammal. In some aspects, the tumor or carcinoma treated is of gastric or ovarian origin. In some implementations, the mammal being treated is a human. The methods may further comprise administering a chemotherapeutic agent.

The invention is also directed to methods of diagnosis, identification, and/or staging of cancer. The methods of diagnosing and/or staging of cancer comprise obtaining a test tissue sample from an individual at risk of having a cancer and a control tissue sample known to be negative for the cancer; and detecting the expression of CDH1 in the test tissue sample and the controls tissue sample with an antibody or subsequence thereof of the invention; wherein the test tissue sample comprises cancer cells where CDH1 expression is reduced compared to the control sample. The methods of identifying cancer stem cells comprises obtaining a test tissue sample from an individual at risk of having a cancer; and detecting the expression of CDH1 in the test tissue sample with an antibody or subsequence thereof of the invention.

BRIEF DESCRIPTION OF THE DRAWINGS

FIG. 2 depicts the prevalence of a proline residue at the linker segment of various transmembrane proteins that enable conformational access to proteases to cleave the sites.

FIG. 3 depicts the amino acid sequence of E-cadherin (SWISS-PROT Accession No. P12830; SEQ ID NO: 14) and indicates the specific peptide antigenic sequence used to produce polyclonal and monoclonal antibodies.

FIG. 13 shows that monoclonal antibodies mAb_VLS02 recognize tumor tissues from patients.

Suspension of treatment still maintained tumor size lower than in controls for up to 50 days after the end of the combined therapy.

DETAILED DESCRIPTION OF THE INVENTION

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

Figure 1:
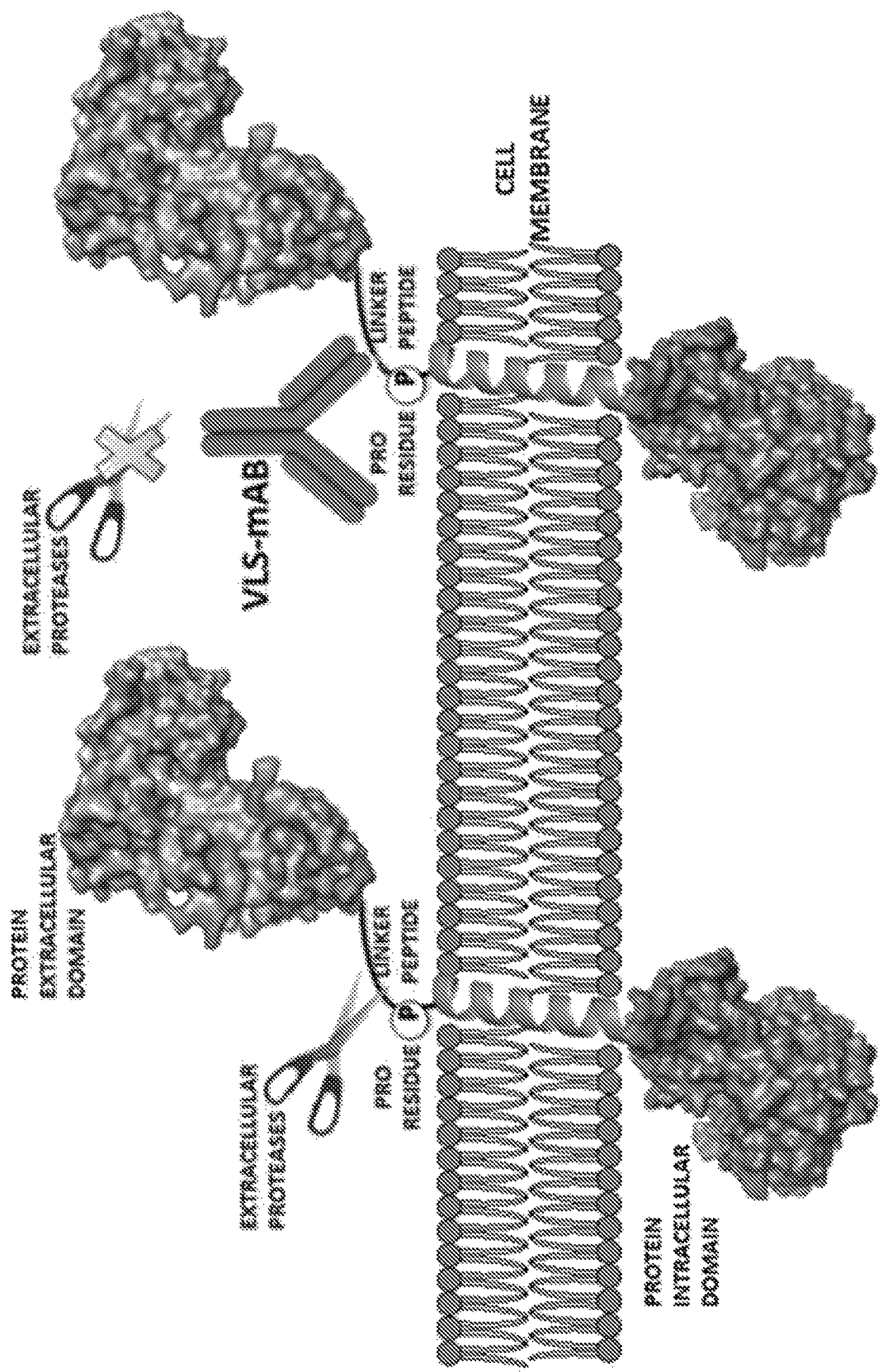
FIG. 1 depicts the mechanism of transmembrane protein extracellular domain shedding promoted by extracellular proteases and the site of action for mAb_VLS02 to block shedding.

Therapeutic monoclonal antibodies usually target cell surface proteins. These surface proteins represent the primary trigger for cellular signaling pathways or links for cell-cell communication. Because of that, cell surface protein shedding plays an important role in cancer progression (FIG. 1). Cell surface shedding is responsible by the disruption of cell-cell interactions, inactivation or transactivation of receptors and stimulation of cancer metastasis. CDH1 (also known as E-cadherin), CD44, EGFR, MHC-I, and integrins are common substrates for protease-activated shedding in cell surface. CDH1 shedding and its downregulation plays also an important role in the epithelial to mesenchymal transition process, which has recently been linked to cancer progression. These observations indicated that additional cleavage of the extracellular domains of CDH1 by metalloproteases is responsible, at least in part, by the disruption of cell-cell interactions in metastatic ovarian cancer. (Sevenich L, Joyce J A. Genes Dev. 2014 1; 28(21): 2331-47). CD44 is another cell surface adhesion receptor highly expressed in many cancers, which regulates metastasis. CD44 shedding and elevated levels of soluble CD44 in the serum of patients is a marker of tumor burden and metastasis in several cancers, including colon and gastric cancer. (Senbanjo and Chellaiah, Front Cell Dev Biol. 7; 5:18, 2017). Although the shedding process not yet fully understood, blocking shedding, for example of CD44, suppresses tumor growth (Škerlová et al, J Struct Biol. August; 191(2):214-223, 2015). Soluble domains of other transmembrane proteins also produce important biological effects during cancer progression, and these shed extracellular domains can be detected in physiological fluids, which makes them potential diagnostic targets (Bryan et al, Br J Cancer. 17; 112(6):1052-1058, 2015; Wilken et al, Biochemistry, 52(26):4531-4340, 2013).

CDH1 is an integral transmembrane glycoprotein that helps maintain epithelial cell-cell adhesion. Like several other transmembrane proteins, E-cadherin full length protein is composed of an extracellular domain, a linker segment connecting the extracellular domain and a single-pass transmembrane region, and a cytoplasmic domain (see Shiraishi et al., J. Immunol. 175(2):1014-1021, 2005). Full-length CDH1 and other transmembrane proteins contain cleavage sites for various extracellular proteases in the linker segment, near the transmembrane domain, and cleavage at these sites produces soluble N-terminal domains. The extracellular soluble domain of E-caderin (sEcad), is found constitutively at low levels in normal, unstimulated epithelial cells and at elevated levels epithelial-derived tumors, such as those in breast, skin, lung, prostate, gastric, ovarian and colorectal cancers (Faca & Hanash, Cancer Res 69:728-730, 2009; Banks et al., J. Clin. Pathol. 48:179-180, 1995; Baranwal et al., Biochem. Biophys. Res. Com. 384(1):6-11, 2009; Chan et al., Gut 48:808-811, 2001; Charalabopoulos et al., Exp. Oncol. 28(1):83-85, 2006; Kuefer et al., Clin. Cancer Res. 9:6447-6452, 2003; Shirahama et al., J. Dermatol. Sci. 13:30-36, 1996; Velikova et al., Br. J. Cancer 77:1857-1863, 1998; Steinhusen U et al, J. Biol. Chem. 276:4972-4980, 2001). While sEcad levels are increased in the urine or serum of cancer patients, the biologic activity of this soluble peptide is not well understood. A number of studies have demonstrated that sEcad disrupts normal epithelial cell-cell adhesion, induces epithelial cell scattering, and enhances tumor cell proliferation, migration, and invasion (Gil et al., Gynecol. Oncol. 108(2):361-369, 2008; Maretzky et al., Proc. Natl. Acad. Sci. USA 102(26): 918279187, 2005; Marambaud et al., EMBO J 21(8):1948-1956, 2002; Najy et al., J. Biol. Chem. 283(26):18393-18401, 2008; Noe et al., J. Cell Sci. 114:111-118, 2001; Ryniers et al., Biol. Chem. 383:159-165, 2002; and Symowicz et al., Cancer Res. 67(5):2030-2039, 2007). The signaling pathways modulating these biologic functions are still unclear.

E-cadherin has also important role in other pathologies. The serine proteases HtrA/DegP secreted by the human gastrointestinal pathogens *Helicobacter pylori* and *Campylobacter jejuni* cleave the mammalian cell adhesion protein E-cadherin to open intercellular adhesions. Infection of epithelial cells by such agent results in a strong E-cadherin ectodomain shedding, which is an important step in bacterial pathogenesis. (Abfalter et al, Cell Commun Signal. 8; 14(1): 30. 2016).

Furthermore, human embryonic and induced pluripotent stem cells shed the 80-kDa extracellular domain of E-cadherin, which providing novel insights into the autocrine and paracrine activities of pluripotent stem cells, with clear implications for their clinical application. (Rosner and Hengstschlager, Stem Cells; 34(9):2443-6, 2016).

Ovarian cancer is one of the most aggressive and lethal epithelial cancers in women. During the metastasis of ovarian cancer, the production of matrix degrading proteinases by tumor cells contributes to the disruption of cell adhesion and cell movement through this mechanism of shedding of adhesion molecules. These mechanisms have been demonstrated in ovarian cancer for ALCAM and for E-cadherin (CDH1), [Rosso O et al. Mol Cancer Res 5: 1246-1253, 2007; Symowicz J et al. Cancer Res 67: 2030-2039, Faca & Hanash, Cancer Res 69:728-730, 2009].

Gastric cancer is one for which there are fewest therapeutics options, although it was the world's third leading cause of cancer mortality in 2012 (responsible for 723,000 deaths). The prognosis of advanced gastric cancer remains poor, and curative surgery is regarded as the only option for cure. In patients with metastatic gastric cancer, median overall survival remains under one year, and standard chemotherapy regimens do not substantially improve the prognosis of the patients. Over 50 years have passed since 5-fluorouracil (5-FU) was developed, but it still plays a key role in the chemotherapeutic regimens for unresectable gastric cancer. The antitumor effects of 5-FU are enhanced when used in combination with cisplatin (CDDP). However since the development of 5-FU, there are limited anticancer agents for treatment of gastric cancer. (Takahashi T et al, *Cancers* 2013, 5, 48-63).

To complicate the treatment of gastric cancer, approximately 20% of gastric tumors have amplification and overexpression of HER2. Although blockade of HER2 signaling has significantly improved the outlook for esophagogastric cancer patients and combinations of anti-HER2 antibodies with other agents can overcome the emergence of resistance during the treatment of these patients, targeting HER2 still remains challenging due to complex biology of this receptor in gastric cancer (Gerson et al, *Expert Opin Investig Drugs;* 26(5):531-540, 2017.

The majority of gastric cancers are associated with infectious agents, including the bacterium *H. pylori*, but more than 120 inherited mutations in the E-cadherin gene (CDH1) have been found to cause hereditary diffuse gastric cancer (HDGC) and have been associated with approximately 80 percent chance of developing gastric cancer. These mutations often lead to the production of an abnormally short, nonfunctional version of the E-cadherin protein or lead to the production of a protein with an altered structure. A lack of E-cadherin impairs cell adhesion, which increase the likelihood that cancer cells will invade the stomach wall and small clusters of cancer cells will metastasize into nearby tissues. (Ferlay, J. et al. GloboCan 2012, CancerBase 11, http://globocan.iarc.fr; The Cancer Genome Atlas Research Network. *Nature*, vol. 513, September, 2014; Richards, F. M. et al. *Hum. Mol. Genet.* 8, 607-610, 1999; Carneiro P. et al. *FEBS Lett.* August 31; 586(18):2981-9, 2012; Corso G. et al, *Cancer Metastasis Rev.* December; 33(4):1081-94, 2014).

The present invention is based, in part, on the discovery that targeting epitopes on cell surface proteins very close to the extracellular membrane in cancer cells results in epithelial-derived tumor growth suppression or tumor regression in cancer. The area of cell surface proteins close to the extracellular membrane is denominated here as the linker segment, which is not necessarily part of the extracellular domains of the transmembrane protein. This invention is also based, in part, on the discovery that several transmembrane proteins that shed their extracellular domains during cancer progression have a proline residue in the linker segment, close to the transmembrane domain that might grant access to extracellular proteases to cleave these sites due to conformational specificities (FIG. 2). Accordingly, one aspect of the invention is directed the generation of antibodies to target the linker segment, in particular the linker segment of important cancer-related proteins such as, but not limited to, CDH1, CD44, EGFR, MHC-I, and integrins. The antigenic peptide for generating such antibodies is a sequence of amino acid less than 30, preferably less than 20, amino acids in length where a proline residue is found within the first 10 amino acids of the sequence (counted according to the convention of writing peptide sequence from the N-terminus to the C-terminus). In some implementations, the antigenic peptide comprises a portion of the linker segment of CDH1. Accordingly, the antigenic peptide comprises VEAGLQIPAC (SEQ ID NO:3), preferably RKAQPVEAGLQIPAC (SEQ ID NO:4). In other implementations, the antigenic peptide comprises a sequence having at least 60% identity to the linker segment, or a portion of the linker segment, of CDH1. These include the linker sequence Thus, the antigenic peptide may comprise a sequence having at least 60%, at least 70%, at least 80%, at least 90% identity to the sequence set forth in SEQ ID NO:1 or SEQ ID NO:2.

Accordingly, this invention also relates to any antibody or subsequence thereof (including Fab, single-chain variable fragment (scFv), and diabodies), immunoreactive fragment of any protein, nucleic acid, carbohydrates or lipids that target or compete with the E-cadherin linker segment or other cell surface shed proteins which also contains the conformational linker peptide having at a least 60% amino acid sequence identity to the linker segment of E-cadherin. In some embodiments, the antibody or subsequence thereof is the antibody produced by the antigenic peptide described above. For example, the antibody or subsequence thereof is produce by an antigenic peptide having the sequence set forth in SEQ ID NO:1, preferably having the sequence set forth in SEQ ID NO:2. In some embodiment, the antibodies or subsequence thereof binds to a region of CDH1 between the extracellular domain and the transmembrane domain, wherein the antibody or subsequence comprises a heavy chain variable region sequence and a light chain variable region sequence identical to a heavy chain variable region sequence and a light chain variable region sequence of an antibody produced by hybridoma cell line VLS-C1G. For example, the antibodies or subsequence thereof comprises heavy chain and light chain variable region complementarity determining regions (CDRs) sequences identical to heavy chain and light chain variable region sequence CDRs of an antibody produced by VLS-C1G. In a preferred embodiment, the antibody or subsequence thereof is the one produced by VLS-C1G. As the nucleic acid for producing the antibodies or portions of the antibodies of the invention may be determined from the hybridoma that produces these antibodies and the amino acid sequence of these antibodies can also be determined using methods known in the art, the invention is also directed to a polypeptide that comprises an amino acid sequence which is substantially the same as the amino acid sequence of the variable region of the monoclonal antibody of the invention as well as the nucleic acid that encodes such a polypeptide. For example, certain embodiments of the invention are directed to polypeptide that comprises an amino acid sequence which is substantially the same as the amino acid sequence of the variable region of the monoclonal antibody produced by VLS-C1G or the nucleic acid that encodes such a polypeptide.

The aforementioned antibodies or subsequence thereof are useful for the treatment of adenocarcinoma, for example from gastric, ovarian or other cancers that express E-cadherin and/or has cleavage site for extracellular proteases leading to shedding. These antibodies block cleavage sites in the linker segment of E-cadherin and/or in the linker segment of other homologous proteins. In some aspects, these antibodies block tumor growth and metastasis in vivo models of gastric and ovarian cancers. For example, the antibodies block E-cadherin and others signal transduction pathways that are critical for tumor growth, invasion, angiogenesis and metastasis. The antibodies or subsequence thereof may be humanized for therapeutic applications. The antibodies are also useful for in vivo imaging of E-cadherin positive tumors and/or for tissue diagnosis and prognosis. In these implementations, the antibody may be labeled with one or more labels selected from the group consisting of a biotin label, a fluorescent label, an enzyme label, a coenzyme label, a chemiluminescent label, and a radioactive isotope label.

The antibodies or subsequence thereof can be used as single agents or in combination with at least one other anti-cancer agent to treat or prevent tumor growth and metastasis. The other anti-cancer agent may be selected from cytotoxic agents, cytostatic agents, anti-angiogenic agents, debulking agents, chemotherapeutic agents, radiotherapy, and radiotherapeutic agents, targeted anti-cancer agents (including both monoclonal antibodies and small molecule entities), biological response modifiers (BRMs), therapeutic antibodies, cancer vaccines, cytokines, hormone therapies, radiation therapy and anti-metastatic agents, or immunotherapeutic agents. In some embodiments, the other anti-cancer agent is an antagonist of parallel or downstream pathways related to tumor growth, such as synergistic signal transduction pathways or those that target downstream or upstream pathways involved in E-cadherin mediated signal transduction. For example, the antibodies may be combined with current therapeutic antibodies, such as trastuzumab. In some implementations, the antibodies or subsequence thereof are used as adjuvants or as therapeutics for existing tumors. Antibodies or subsequence thereof targeting the linker segment can be used in combination with other antibodies against E-cadherin to block multiple domains of the E-cadherin protein.

In practicing combination therapy, the antibodies or subsequence thereof and the other anti-cancer agent may be administered to the subject simultaneously, either in a single composition, or as two or more distinct compositions using the same or different administration routes. Alternatively, the antibodies or subsequence thereof may precede, or follow, the other anti-cancer agent treatment by, e.g., intervals ranging from minutes to weeks. The time period between each delivery is such that the other anti-cancer agent and antibodies or subsequence thereof are able to exert a combined effect on the tumor. In some embodiments, both the other anti-cancer agent and the antibodies or subsequence thereof are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the antibodies or subsequence thereof and the other anti-cancer agent. The combination therapy may be administered once, twice or at least for a period of time until the condition is treated, palliated or cured. In some embodiments, the combination therapy is administered multiple times, for example, three times daily, once daily, once every month, or once every six months. The administering may be on a schedule such as three times daily, twice daily, once daily, once every two days, once every three days, once weekly, once every two weeks, once every month, once every two months, once every three months, once every six months or may be administered continuously via a pump. The combination therapy may be administered via any route. The combination therapy may be administered at a site distant from the site of the tumor.

In one embodiment, the antibodies or subsequence thereof is administered in combination with at least one other anti-cancer agent for a short treatment cycle to a subject in need thereof. The invention also contemplates discontinuous administration or daily doses divided into several partial administrations. The antibodies or subsequence thereof and the other anti-cancer agent may be administered interchangeably, on alternate days or weeks; or a sequence of antibody treatments may be given, followed by one or more treatments of other anti-cancer agent therapy. As will be understood by those of ordinary skill in the art, the appropriate doses of antibodies or subsequence thereof and the other anti-cancer agent will be generally around those already employed in clinical therapies wherein these therapeutics are administered alone or in combination with other anti-cancer therapeutics.

The invention also contemplates the use of the antigenic peptides for generating the antibodies of the invention as a therapeutic agent for inhibiting the activity of metalloproteases. As shown in example 7, a synthetic peptide comprising the sequence set forth in SEQ ID NO:1 (VEA-GLQIPA) inhibited the activity of a metalloproteases. Accordingly, synthetic peptides comprising at least a portion of the linker segments of transmembrane proteins (such as the antigenic peptides for generating the antibodies or subsequence thereof the present application), are also useful to prevent shedding of the transmembrane proteins. In one implementation, the synthetic sequence comprising the sequence set forth in SEQ ID NO:4 inhibits the cleavage activity of MMP9. These peptides may also be used in combination with anti-cancer agents to aid the inhibition of tumor proliferation and progression and prevent or inhibit oncogenesis by inhibiting the shedding process.

Antibodies include subsequences (e.g., fragments) and modified forms (e.g., sequence variants) as set forth herein. An "antibody" subsequence refers to a functional fragment or subsequence of immunoglobulin molecule. In particular embodiments, antibody subsequences include an Fab, Fab, F(ab)2, Fd, Fv, single-chain Fvs (scFv), disulfide-linked Fvs (sdFv) and VL or VH domain fragments. In particular aspects, an Fab, Fab' and F(ab')2, Fd, Fv, single-chain Fvs (scFv), disulfide-linked Fvs (sdFv) and VL or VH domain subsequence. In additional aspects, an Fab, Fab' and F(ab')2, Fd, Fv, single-chain Fvs (scFv), disulfide-linked Fvs (sdFv) and VL or VH domain subsequence has substantially the same or has the same binding affinity or binding specificity, or one or more functions or activities of the disclosed antibody. The terms "functional subsequence" and "functional fragment" when referring to an antibody of the invention refers to a portion of an antibody that retains at least a part of one or more functions or activities as an intact reference antibody.

CDH1 binding antibody subsequences, including single-chain antibodies, can include all or a portion of heavy or light chain variable region(s) (e.g., CDR1, CDR2 or CDR3) alone or in combination with all or a portion of one or more of the following: hinge region, CH1, CH2, and CH3 domains. Also included are antigen-binding subsequences of any combination of heavy or light chain variable region(s) (e.g., CDR1, CDR2 or CDR3) with a hinge region, CH1, CH2, and CH3 domains.

CDH1 binding antibody subsequences (e.g., Fab, Fab', F(ab')2, Fd, scFv, sdFv and VL or VH) can be prepared by proteolytic hydrolysis of the antibody, for example, by pepsin or papain digestion of whole antibodies. Antibody fragments produced by enzymatic cleavage with pepsin provide a 5 S fragment denoted F(ab')2. This fragment can be further cleaved using a thiol reducing agent to produce 3.5 S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., Methods Enymol. 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the H3L/H3L homolog antibody gene into a host cell such as Cos cells or *E. coli*. The recombinant host cells synthesize intact or single antibody chain, such as scFv (see, e.g., Whitlow et al., In: Methods: A Companion to Methods in Enzymology 2:97 (1991), Bird et al., Science 242:423 (1988); and U.S. Pat. No. 4,946,778). Single-chain Fvs and antibodies can be produced as described in U.S. Pat. Nos. 4,946,778 and 5,258,498; Huston et al., Methods Enzymol. 203:46 (1991); Shu et al., Proc. Natl. Acad. Sci. USA 90:7995 (1993); and Skerra et al., Science 240:1038 (1988).

Additional modifications of antibodies included in the invention are antibody additions (derivatives)/insertions. For example, an addition can be the covalent or non-covalent attachment of any type of molecule to the antibody. Specific examples of antibody additions and derivatives include glycosylation, acetylation, phosphorylation, amidation, formylation, ubiquitinatation, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified antibody having an amino acid addition is one in which a second heterologous sequence, i.e., heterologous functional domain is attached (covalent or non-covalent binding) that confers a distinct or complementary function upon the antibody. Such sequences can be referred to as chimeric sequences. For example, an Fc region can be a chimera that includes portions of human IgG1 and IgG3 Fc regions, which provides the antibody with increased complement fixation as compared to an antibody with an IgG1 or IgG3 Fc. In another example, an amino acid tag such as T7 or polyhistidine can be attached to antibody in order to facilitate purification or detection of antigen. Yet another example is a toxin attached to an antibody in order to target cancerous cells for killing, proliferation inhibition, replication inhibition, etc. Thus, in other embodiments the invention provides antibodies and a heterologous domain, wherein the domain confers a distinct function, i.e. a heterologous functional domain, on the antibody.

It should be noted that there are currently no clinically approved therapies or diagnostics targeting E-cadherin or the downstream beta-catenin pathway. Few drug candidates targeting this pathway have succeeded in clinical trials. Additionally, these drug candidates have shown no activity in the preclinical models where the antibodies of the present invention have demonstrated activity (see, e.g., Zhong et al., Tumor Biology, 36: 6139 (2015), and Kahn, Nature Rev. Drug Disc. 13: 513 (2014)). These examples show the clear superiority of the design approach for developing antibodies against transmembrane proteins with crucial roles in the development of cancer and the superiority of the antibodies or subsequence thereof and peptides designed using this approach. In particular, none of the antibodies against E-cadherin known in the prior art inhibits shedding of sECAD.

In certain aspects, the present invention is related to an antibody or fragment (or any other affinity reagent) thereof capable of binding to a region composed of a peptide segment between the transmembrane domain and the extracellular domain of cell surface proteins, which would be cleaved during proliferative diseases.

In other aspects, present invention is directed to an antibody or fragment (or any other affinity reagent) thereof capable of binding to a region composed of a peptide segment between the transmembrane domain and the extracellular domain of proteins shed from cell surface by extracellular proteases during proliferative disease.

In some aspects, the present invention relates to an antibody or fragment (or any other affinity reagent) thereof capable of binding to pre-malignant cells expressing e-cadherin and thereof preventing cell spreading or metastasis.

In one aspect, the present invention is directed to an epitope composed of 5 to 20 amino acids present between the transmembrane domain and extracellular domain of proteins shed from cell surface by extracellular proteases. In another aspect, the present invention relates to an epitope composed of 5 to 20 amino acids present between the transmembrane domain and extracellular domain of proteins shed from cell surface by extracellular proteases, which contains a proline residue between amino acids 1 to 10 in the sequence.

In some embodiments, the present invention is directed to a hybridoma cell line, named VLS_C1G, that produces antibodies against peptide pep_VLS02 deposited at the American Type Culture Collection having ATCC Accession No. PTA-124082. In other embodiments, the present invention relates to an antibody produced by the disclosed hybridoma cell line.

In yet other embodiments, the present invention is directed to a hybridoma cell line producing antibodies against VLS03 and/or an antibody produced by such a hybridoma cell line.

In one aspect, the present invention relates to an antibody or fragment or any other affinity reagent thereof capable of binding to domain 5 of E-cadherin, the same antigenic determinant of E-cadherin, in vivo or in vitro, as does the monoclonal antibody produced by the hybridoma cell deposited at the American Type Culture Collection having ATCC Accession No. PTA-124082.

In other aspects, the antibodies of the present invention are humanized or fully human. In yet other aspects, the disclosed antibody is a diabody or scFv.

In one implementation, the present invention is directed to an antibody or fragment thereof capable of binding to cleavage site of E-cadherin, the same antigenic determinant of E-cadherin, in vivo or in vitro, as does the monoclonal antibody produced by the hybridoma cell deposited at the American Type Culture Collection having ATCC Accession No. PTA-124082.

In another implementation, the present invention is directed to a method of inhibiting the growth of cancer cells, the method comprising the step of: administering an antibody or fragment thereof as disclosed herein, wherein the cancer cells express or overexpress E-Cadherin, and wherein the antibody inhibits the growth of cancer cells.

In some aspects, the cancer cells are gastric cancer cells. In other aspects, the cancer cells are ovarian cancer cells. In yet other aspects, the cancer cells are lung cancer cells, or pancreatic, breast, colon or any cancer tissue expressing E-cadherin.

In some embodiments, the present invention is directed to a method of treating a cancer patient, comprising the steps of: (a) obtaining a test tissue sample from an individual at risk of having a cancer that expresses an E-cadherin protein; (b) determining the presence or absence or amount of the E-cadherin protein in the test tissue sample in comparison to a control tissue sample known to be negative for the cancer; thereby diagnosing said cancer that expresses a E-cadherin protein, wherein the E-cadherin protein is expressed at normal or low levels, or is expressed by a subset of cells, or is overexpressed; and (c) administering an effective amount of E-cadherin antibody or fragment as disclosed herein to the individual at risk of having a cancer that expresses a E-Cadherin protein. In certain aspects, the tissue sample is gastric or ovarian tissue.

In certain aspects, the antibody inhibits the growth of circulating cancer cells and/or cancer cells in a tumor. In other aspects, the cancer is gastric cancer or ovarian cancer. In some aspects, the cancer is a metastatic cancer.

In some implementations, the present invention is directed to a method of diagnosing a cancer patient, comprising the steps of: (a) obtaining a test tissue sample from an individual at risk of having a cancer that expresses a E-cadherin protein; or nucleic acid (mRNA); (b) determining the presence or absence or amount of the E-cadherin protein in the test tissue sample in comparison to a control tissue sample known to be negative for the cancer by contacting a sample with an effective amount of E-cadherin antibody or fragment as disclosed herein; thereby diagnosing said cancer that expresses a E-cadherin protein, wherein the E-cadherin protein is expressed at normal or low levels, or is expressed by a subset of cells, or is overexpressed.

In other implementations, the present invention relates to a method of identifying cancer stem cells, comprising the steps of: obtaining a test tissue sample from an individual at risk of having a cancer that expresses a E-cadherin protein; determining the presence or absence of cancer stem cells or circulating tumor cells in the test tissue sample in comparison to a control tissue sample known to be negative for the cancer; wherein the E-cadherin protein is expressed at normal or low levels, or is expressed by a subset of the stem cells and is not overexpressed, using the antibodies disclosed herein.

E-cadherin has been shown to be expressed in breast cancer, carcinoid, cervical cancer, colorectal cancer, endometrial cancer, head and neck cancer, liver cancer, lung cancer, melanoma, ovarian cancer, pancreatic cancer, prostate cancer, renal cancer, skin cancer, stomach cancer, testis cancer, thyroid cancer, and urothelial cancer (see the data available for the antibody AMAb90863 that binds to the epitope $^{592}$APIPEPRTIF$^{602}$ on the extracellular domain of CDH1 available at the Human Protein Atlas; see www.proteinatlas.org). Accordingly, the compositions and methods of the present invention may be used to identify, diagnose, and/or treat various cancers including, but not limited to, breast cancer, carcinoid, cervical cancer, colorectal cancer, endometrial cancer, head and neck cancer, liver cancer, lung cancer, melanoma, ovarian cancer, pancreatic cancer, prostate cancer, renal cancer, skin cancer, stomach cancer, testis cancer, thyroid cancer, and urothelial cancer. In some embodiments, the cancer is of epithelia origin (i.e., adenocarcinoma). In other embodiments, the cancer is a HER2-positive tumor.

Accordingly, the invention provides compositions and methods that target E-Cadherin in the diagnosis, prognosis, and treatment of proliferative diseases such as but not limited to epithelial pre-metastatic and metastatic cancers expressing E-Cadherin or other cleavable cell surface protein.

DEPOSIT INFORMATION

The following biological material has been deposited under the terms of the Budapest Treaty with the American Type Culture Collection (ATCC®), 10801 University Boulevard, Manassas, Va. 20110-2209, and given the following accession number:

| Deposit | Accession Number | Date of Deposit |
|---|---|---|
| Murine hybridoma; VLS-C1G | PTA-124082 | May 4, 2017 |

The hybridoma cell line has been deposited under conditions that assure that access to the culture will be available during the pendency of this patent application to one determined by the Commissioner of Patents and Trademarks to be entitled thereto under 37 C.F.R. § 1.14 and 35 U.S. C. § 122. The deposit represents a substantially pure culture of the deposited hybridoma cell line. The deposit is available as required by foreign patent laws in countries wherein counterparts of the subject application or its progeny are filed. All restrictions imposed by the depositor on the availability to the public of the deposited material will be irrevocably removed on the granting of a patent except as permitted under 37 CFR 1.808(b). However, it should be understood that the availability of a deposit does not constitute a license to practice the subject invention in derogation of patent rights granted by governmental action.

The following examples are given for purely illustrative and non-limiting purposes of the present invention.

EXAMPLES

Figure 4:
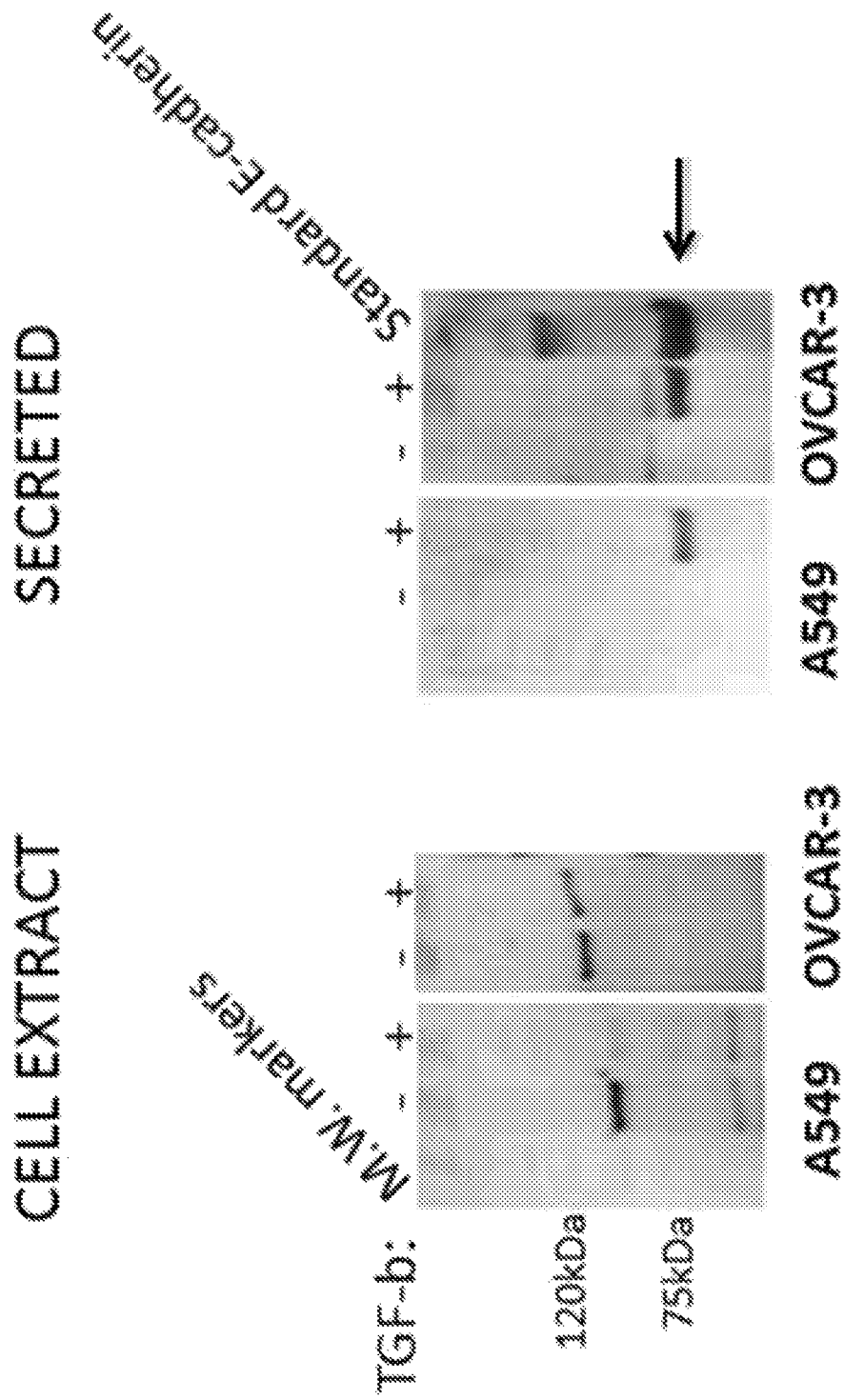
FIG. 4 depicts E-cadherin extracellular domain shedding detected in cancer cells.

Example 1. Detection of E-Cadherin Extracellular Domain Shedding in Cancer Cells To determine whether differences exist in the levels of sEcad released after simulating metastasis by the induction of Epithelial to Mesenchymal Transition (EMT) between different cells lines utilized as tumor progression models for validation and elucidation of our candidate antibodies, it was performed the detection of the intact form (E-Cad, cell extract) and cleaved (sEcad, culture supernatant) form of E-cadherin. Differences in the amount of cadherin before and after treatment with TGF-β (EMT inducer) were observed by Western blot analysis. The commercial polyclonal antibody to E-cadherin was purchased from R&D systems. As expected, there was an increase in the level of soluble cadherin or cleaved (sECAD) in the culture supernatant (~75 kDa) and decrease in intact transmembrane cadherin (ECAD) in total cell extract (~120 kDa) (FIG. 4).

Example 2. Design and Synthesis of the Antigenic Peptides

The production of antibodies against the target protein neo-epitopes was initiated based on literature data aided by bioinformatics analysis of protein structure. The work published by Marambaud et al. demonstrated that the cleavage sites on E-cadherin (CDH1) for metalloproteases, which results in the release of the extracellular domain, is located between residues 700 (Pro) and 701 (Val) (FIG. 2). This cleavage site is located between the fifth extracellular domain and the transmembrane region. To make predictions with different algorithms, the complete amino acid sequence of E-cadherin, which contains 882 amino acids, was reduced to a string of only 289 amino acids. This shorted string of amino acids corresponds to domain 5 and contains the cleavage site region transmembrane and the intracellular domain.

Figure 5:
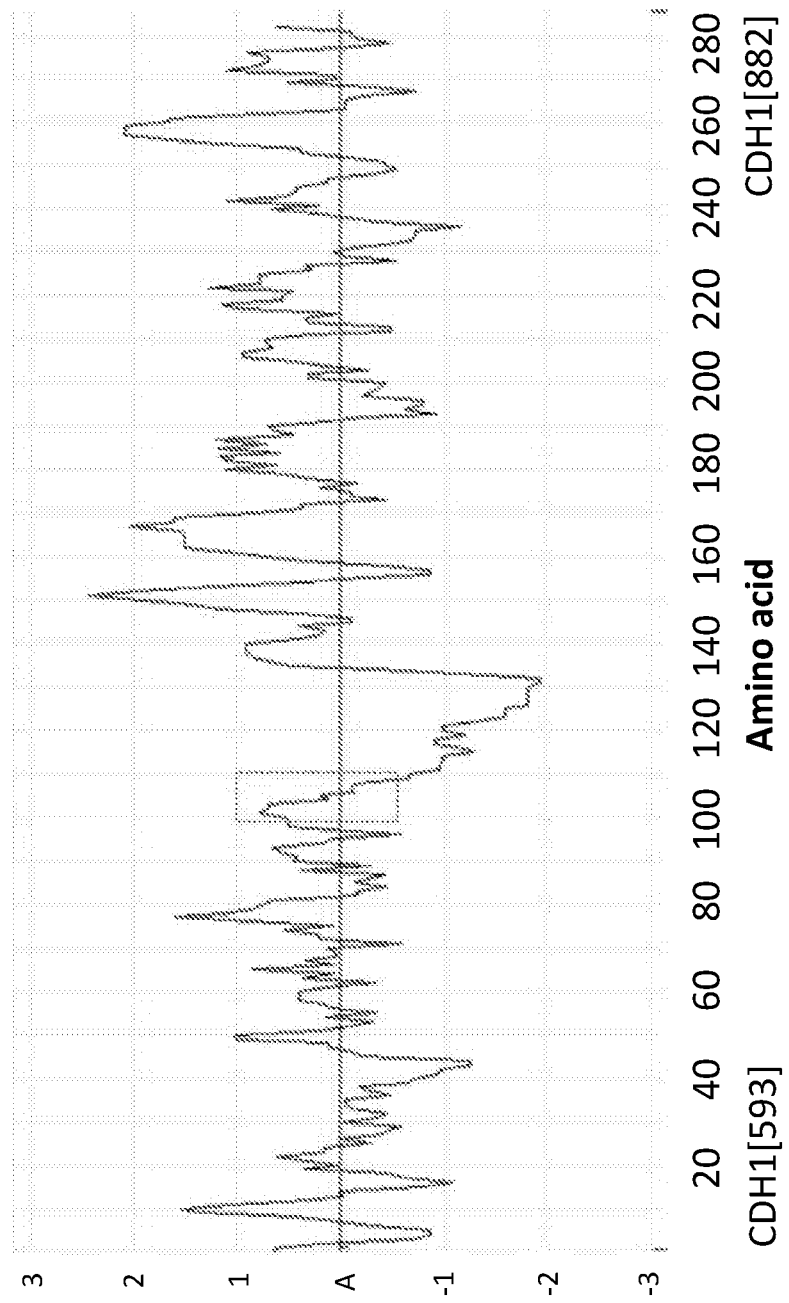
FIG. 5 depicts the location of the antigenic E-cadherin linker segment in the amino acid sequence of the protein.

First, we evaluated the position of the transmembrane region by TMHMM algorithm, then we predicted the secondary structures using APSSP2 and antigenicity using an algorithm called Hopp and Woods, which considers the local hydrophilicity as a determining point of antigenicity. FIG. 5 shows the region containing a metalloprotease cleavage site (highlighted by dashed rectangle) shows antigenicity above average for the sequence. By combining all these predictions, we concluded that the region containing a metalloprotease cleavage site (1) is located in a solvent accessible area, (2) corresponds to a loop or strap that connects two stable secondary structures (domain 5 and transmembrane helix), and (3) shows antigenic potential. All these features of a peptide antigen are important to obtain a functional antibody, which recognizes not only a linear sequence but also the sequence within a three-dimensional structure. Added to all this, we observed that a proline residue after transmembrane domain is present in many proteins on the cell surface that are targets for proteolytic processing, and all of these proteins represent important targets for cancer therapy (FIG. 2). We believe that this special amino acid in that position imposes a steric advantage that gives access for metalloproteases binding, which promote cleavage. Therefore, we believe that this characteristic may also important to provide accessibility to an antibody that binds to this region. Thus we produced synthetic peptides of 15 amino acids covering the cleavage site sequence of E-cadherin and having the conserved proline residue plus a cysteine residue at the end, which facilitates peptide conjugation. These peptides were then used for the production of antibodies.

Figure 6:
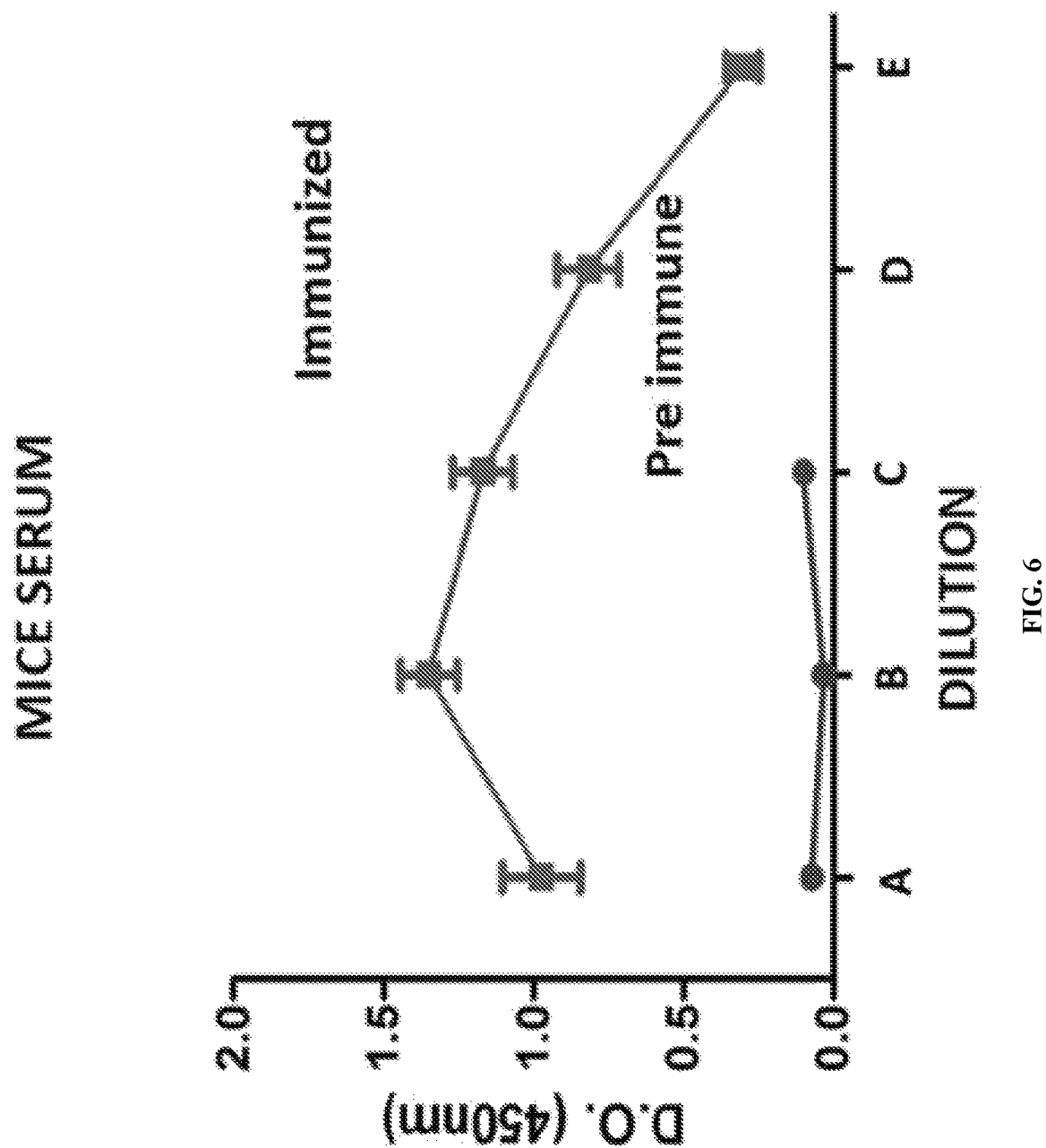
FIG. 6 depicts the antigenic ability of the E-cadherin linker segment and the production of polyclonal antibodies pAb_VLS02 targeting the E-cadherin linker segment. The dilutions shown are: A) 1:20; B) 1:200; C) 1:2000; D) 1:20000; and E) 1:200000.

Example 3. Production and Antigenic Ability of Antibodies Clones Targeting E-Cadherin Linker Segment Polyclonal antibodies against synthetic peptides pep_VLS02 (RKAQPVEAGLQIPAC; SEQ ID NO: 4) and pep_VLS03 (VEAGLQIPAC; SEQ ID NO: 3) were produced according to methods known in the art. The "pool" of immunized mice sera was analyzed and showed reactivity above the dilution 1:20,000. The immunized sera had significantly higher absorbance than the pre-immune sera at dilutions up to 1/20,000, indicating a constant high affinity (FIG. 6). These results confirmed the immunogenic capacity of pep_VLS02 and pep_VLS03 and demonstrated the effectiveness of the immunization process.

Figure 7:
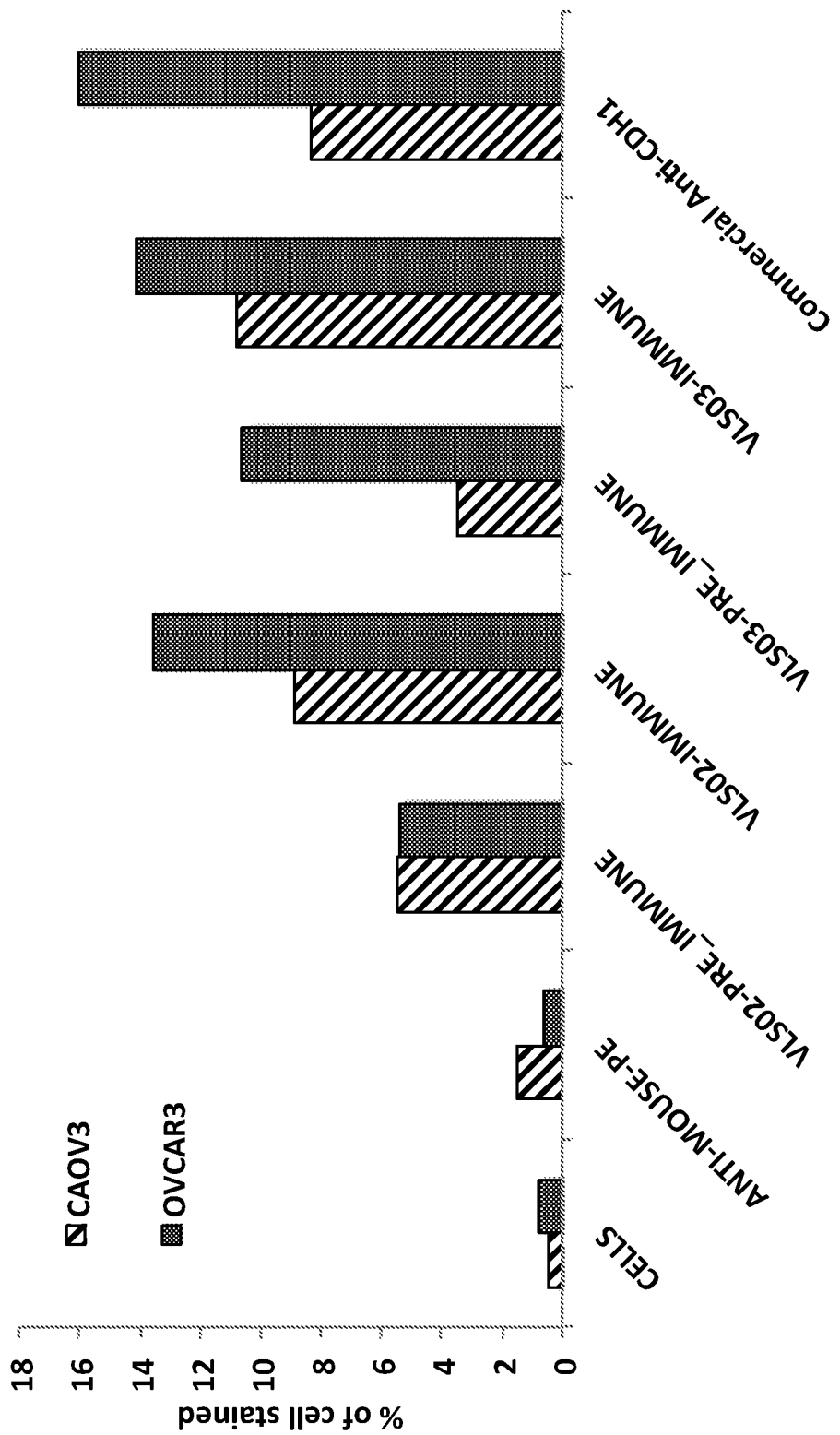
FIG. 7 shows that polyclonal antibodies pAb_VLS02 recognize cancer cells.

Example 4. Antibodies Clones Against E-Cadherin Linker Segment Recognize Cancer Cells Confluent CaOV3 and OVCAR3 were incubated in the presence or absence of antibodies clones directed against E-cadherin (pAb_VLS02 or pAb_VLS03) or in the presence of pre-immune serum and analyzed with fluorescence-activated cell sorting (FACS). Both antibodies exhibited a marked increase in binding capability to CaOV3 and OVCAR3 cancer cells when compared to the pre-immune control condition. A similar rate of binding of pAb_VLS02 or pAb_VLS03 to CaOV3 and OVCAR3 cancer cells was seen when compared to commercial monoclonal antibody specific for the extracellular domain of CDH1 (R&D Systems) (FIG. 7).

Example 5. Antibodies Clones Recognize E-Cadherin on the Surface of OVCAR3 and MCF-7

Figure 8:
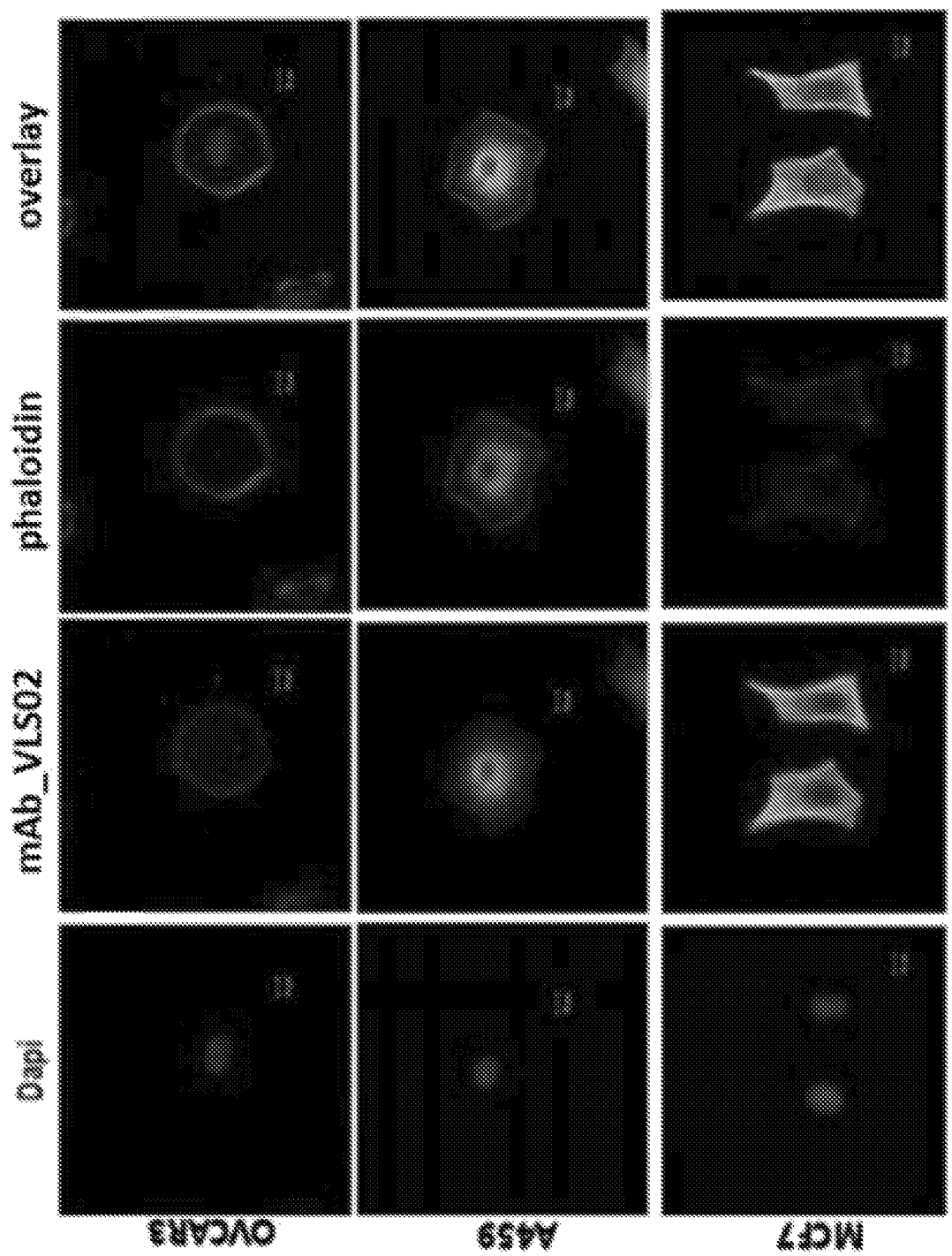
FIG. 8 depicts that polyclonal antibodies pAb_VLS02 recognize E-Cadherin on the surface of ovarian (OVCAR3) and breast (MCF-7) cancer cells.

Cancer cells lines A549, OVCAR-3, and MCF7 were grown on glass coverslips, fixed in 100% methanol and incubated with pAb_VLS02 for 60 minutes. E-cadherin indirect immunofluorescence staining was performed with Alexa Fluor™ 488 goat anti-mouse IgG for 30 min, and subsequent phalloidin staining was performed with Alexa Fluor™ 594 phalloidin for F-actin. DAPI was used to label nuclei. Analysis and photography were performed on a LSM 710 ZEIZZ confocal microscope with 63× magnification at excitation wavelengths of 543 and 488 nm. FIG. 8 clearly shows that the pAb_VLS02 stained E-cadherin at the plasma membrane.

Example 6. Antibodies Clones Inhibited the Morphological Changing from Normal Aspect (Epithelial) to the Fibroblastoid Aspect (Metastatic) of Cells In human epithelial metastatic cancer, it has been demonstrated that epithelial-mesenchymal transition (EMT) occurs and is related to invasiveness and metastasis (Wan L, Pantel K & Kang Y, 2013; Bhowmick N A et al. 2004; Boyer B. et al. 2000). EMT is characterized by loss of epithelial cell-cell contacts by the suppression of components that build up junctional complexes, such as E-cadherin, ZO-1, CAR, occludin, claudin-1 and claudin-7 (Moustakas & Heldin, 2009). Cells that underwent EMT become capable of detaching from each other and moving away from the organized epithelial tissue. EMT can be induced by different stimuli with transforming growth factor (TGF) β signaling having a key role.

Figure 9:
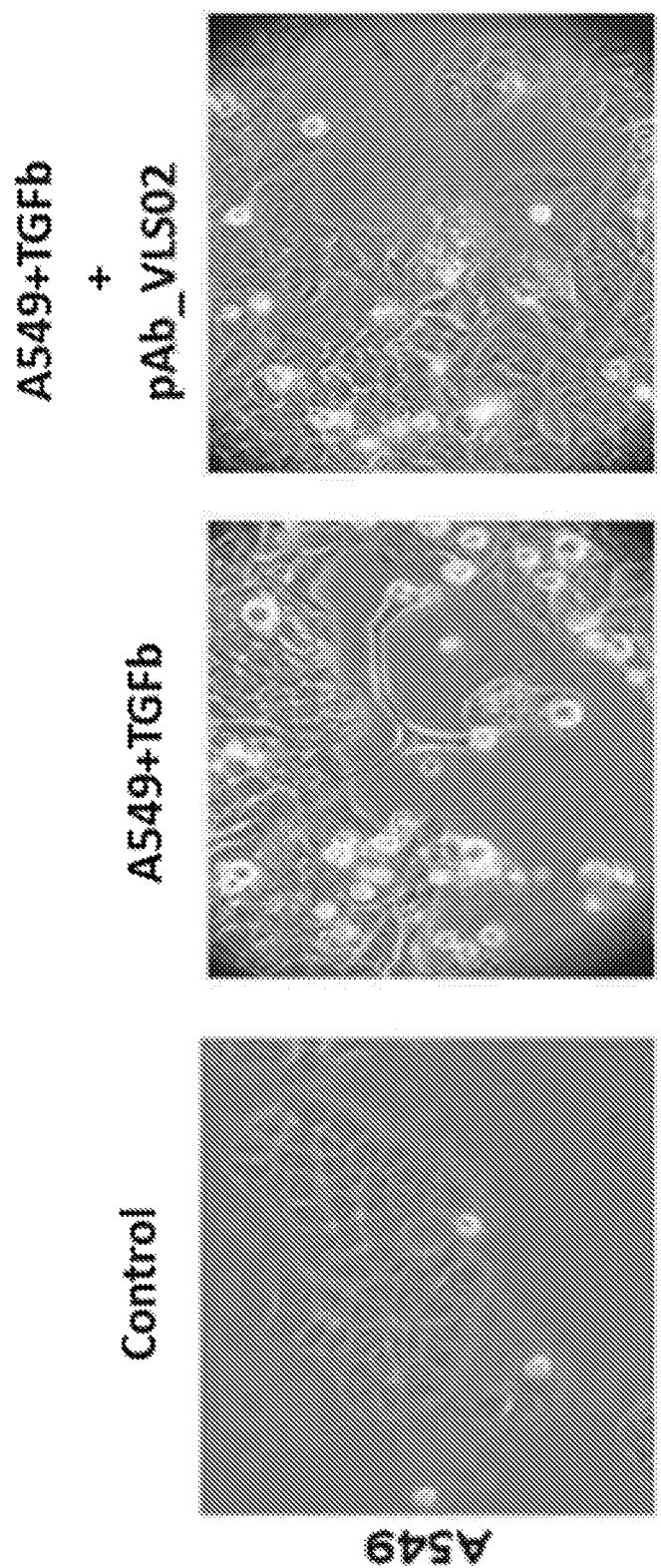
FIG. 9 shows that polyclonal antibodies pAb_VLS02 inhibited the morphological changes that demonstrate the transition of cells from normal (epithelial) to the fibroblastic (metastatic).

Thus, induction of EMT process by TGF-β has been used here as tumor progression model for validation and elucidation of antibodies. The cell line A549 (lung cancer from Sigma) were cultured in DMEM medium (Invitrogen) supplemented with 10% FBS and treated with TGF-β (10 ng/ml) for 72 hours. FIG. 9 shows obvious morphological changes after treatment with TGF-β including alterations of shape and size as well as loss of intracellular contacts, promoting a fusiform fibroblast-like shape, characteristic of metastatic cancer cells. When our pAb_VLS02 was added, the distinctive morphological changes characteristic of metastatic cells were inhibited (FIG. 9).

Figure 10:
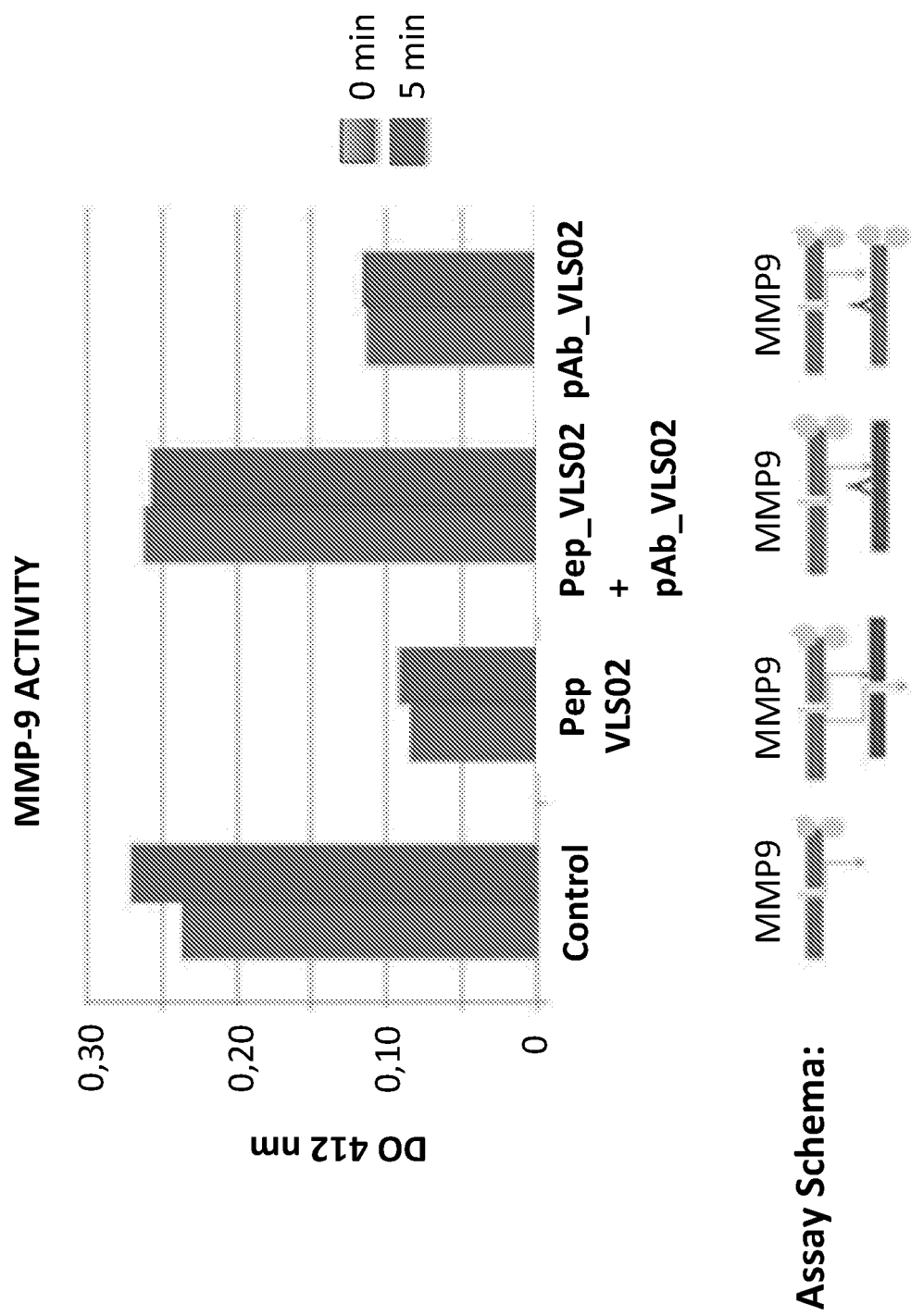
FIG. 10 shows that polyclonal antibodies pAb_VLS02 and peptide pep_VLS02 inhibit E-cadherin cleavage by a metalloprotease.

Example 7. Antibodies Clones and Peptides Inhibit E-Cadherin Cleavage by Metalloprotease The synthetic peptide pep_VLS02 was used as a competitive inhibitor of MMP-9. The MMP-9 enzymatic activity is reduced in the presence of synthetic peptide (FIG. 10). The inhibitory effect of pep_VLS02 against cleavage of E-cadherin opens a new window for the development of new inhibitors.

On the other hand, when the polyclonal antibody pAb_VLS02 is added to the assay, in the presence of its corresponding peptide, the MMP-9 activity was reestablished (FIG. 10). Thus, pep_VLS02 and its correspondent polyclonal antibody modulate MMP-9 activity and inhibit the E-cadherin cleavage.

Example 8. Monoclonal Antibody Targeting E-Cadherin-Related Peptide

Figure 11:
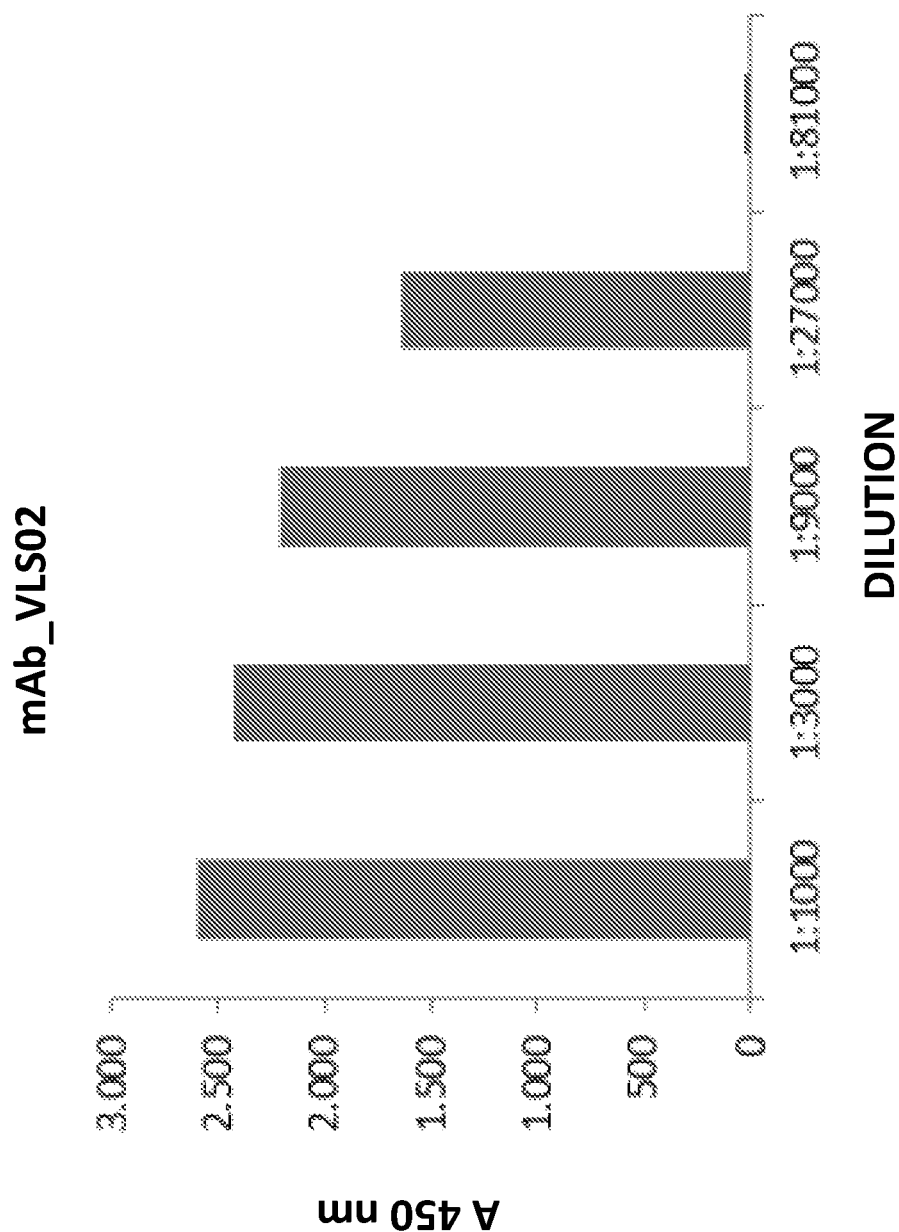
FIG. 11 shows the titration of monoclonal antibodies mAb_VLS02 targeting the E-cadherin linker segment.

The peptide pep_VLS02 was used for the production of the novel monoclonal antibody. To test the binding specificity of the mAb_VLS02 to its antigen, a titration curve at varying antibody dilutions was performed (FIG. 11). The mAb_VLS02 was able to produce strong chemoluminescent signals at dilutions up to 1:27000, which indicates a very strong binding constant and specificity for the antigen. We obtained 8 strains of hybridomas producing monoclonal antibodies with similar activity. One milligram of the monoclonal antibody mAb_VLS02, can be obtained from 5 ml of supernatant produced by the hybridoma cell line VLS-C1G (ATCC Accession No. PTA-124082).

Example 9. Monoclonal Antibodies Reduce the Cell Motility of Cancer Cells

Figure 12:
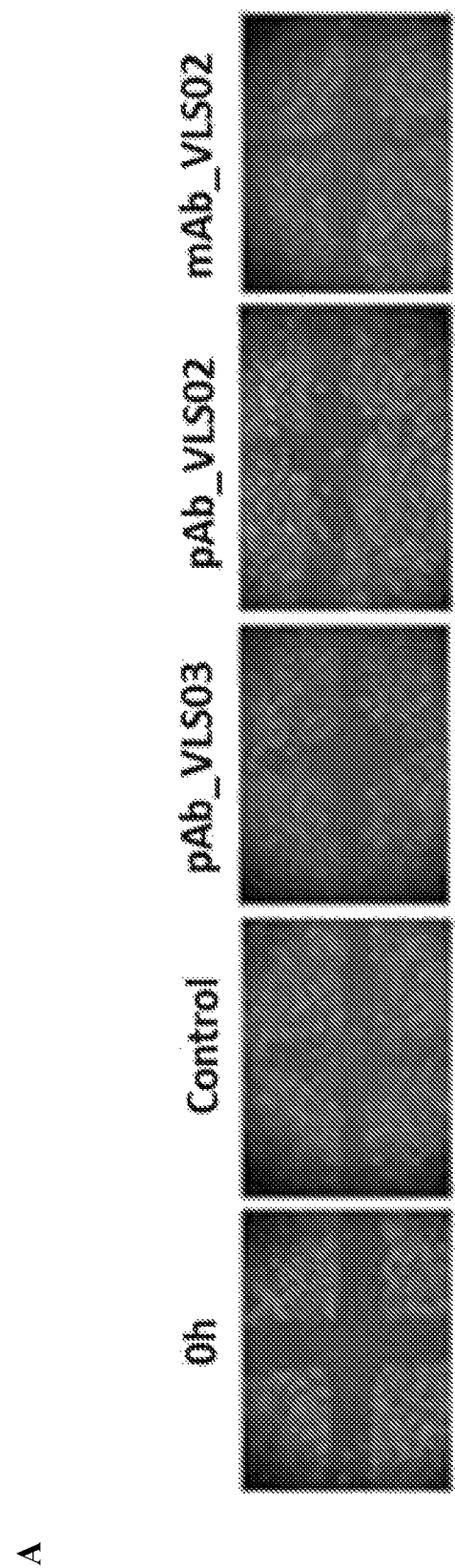
FIGS. 12A and 12B show that monoclonal antibodies mAb_VLS02 reduce the cell motility of cancer cells.
Figure 12:
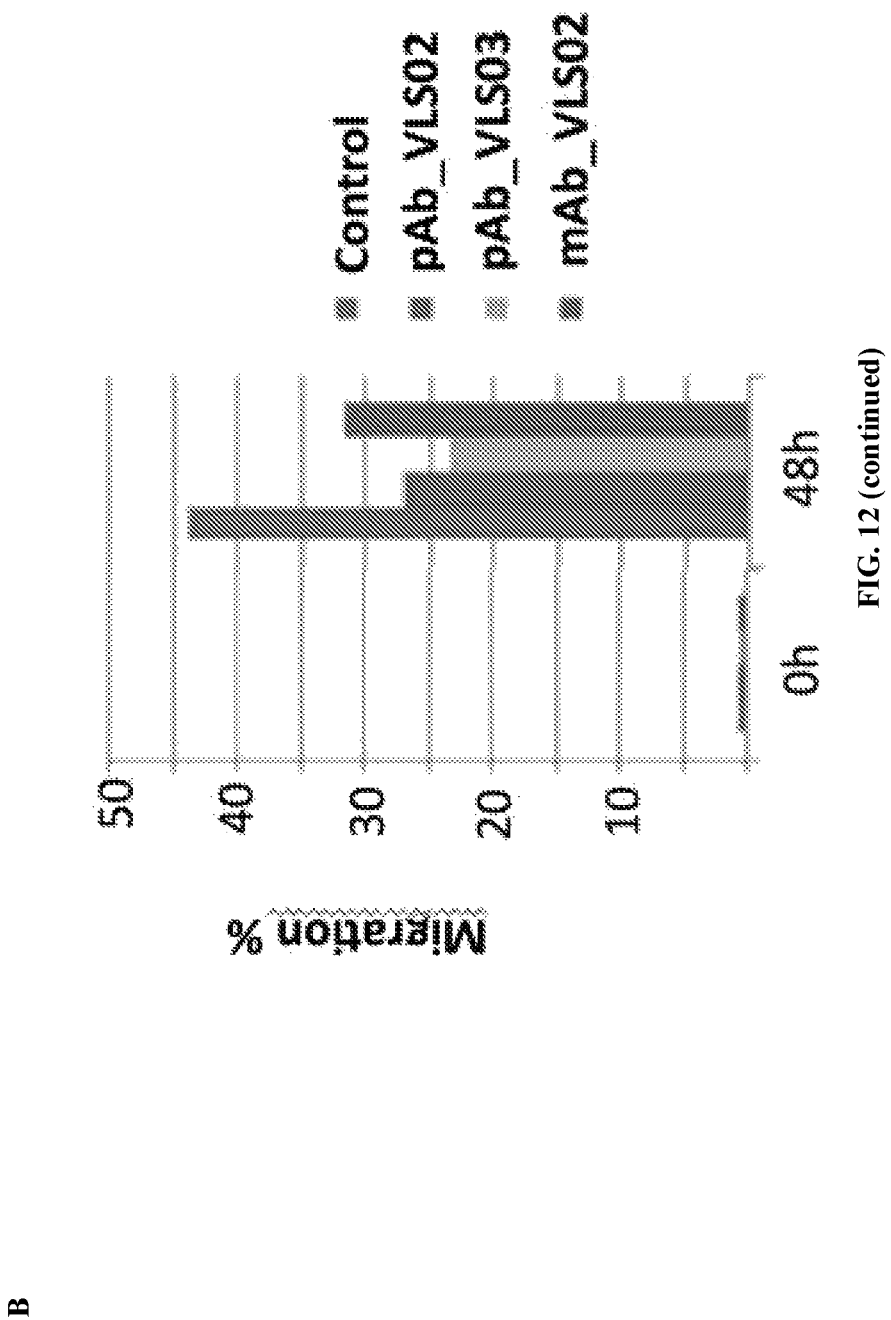

We performed a wound-healing assay, which showed that antibodies against pep_VLS02 and against pep_VLS03 could reduce the in vitro motility of metastatic cells (A549), another characteristic of metastasis process. A549 cells were grown in 12-well plates in DMEM with 10% fetal bovine serum (FBS) until confluence. Once the cells reached confluence, they were incubated for 24 hours with the polyclonal pAb_VLS02 or pAb_VLS03 or monoclonal antibody mAb_VLS02, in DMEM only. A wound was created in the center of the cell monolayers by a sterile pipette tip. The photographed images were captured 48 hours after creation of the wound (FIG. 12A, left panel). The analysis was performed considering 100% wound size at the time of culture and using ImageJ (NCBI). Wound size analysis performed at 48 hours after creation of the wound revealed that our antibodies inhibit the motility of the metastatic A549 cells (FIG. 12B, right panel).

Example 10. Monoclonal Antibodies Recognize Tumors Tissue from Patients

Titrations were performed with progressive rate of antibody mAb_VLS02 and testing of tissue fixed in formalin and immersed in paraffin (FFPE) of lung cancer (large cell carcinoma). A TMA (tissue matrix arrangement) was made with 01 core control tissue (non-neoplastic liver) and 06 cores of 2 mm from 2 different sites carcinomas: ovary (FIG. 13 Panels B and C) and lung (FIG. 13 Panels A and D). The reactions were performed with negative control (no antibody but with other reagents maintained). Immunostaining was observed mainly in the membrane of malignant cells, and particularly in ovarian carcinoma core.

Example 11. Monoclonal Antibodies have Showed no Toxicity in Animal Models

Figure 14:
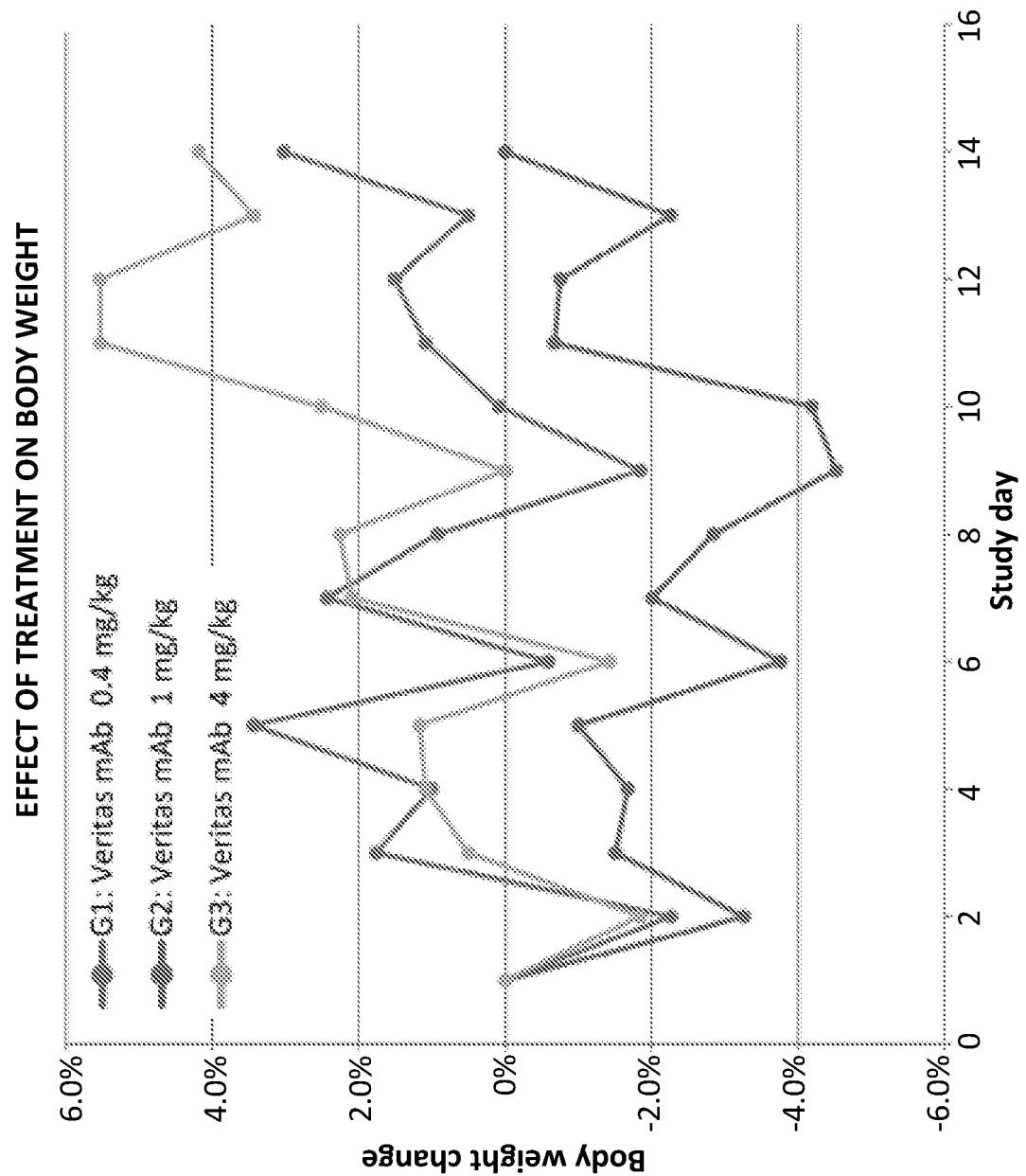
FIG. 14 shows monoclonal antibodies mAb_VLS02 produce no toxicity in animal models, as represented by the antibody's effect on body weight.

Tolerability of monoclonal antibodies mAb_VLS02 of the present application as a single agent was studied in non-tumor-bearing athymic nude mice. The tested intraperitoneal administration doses (0.4, 1.0, and 4.0 mg/kg) were well tolerated, and there was no mortality of animals under the conditions tested in this study. The monoclonal antibodies of the present application when administered at a higher dose of 10 mg/kg or in combination with HERCEPTIN® (trastuzumab) also did not significantly affect the body weight of the tested animals (FIG. 14).

Example 12. Monoclonal Antibodies Inhibit Tumor Growth in Animal Models

Figure 15:
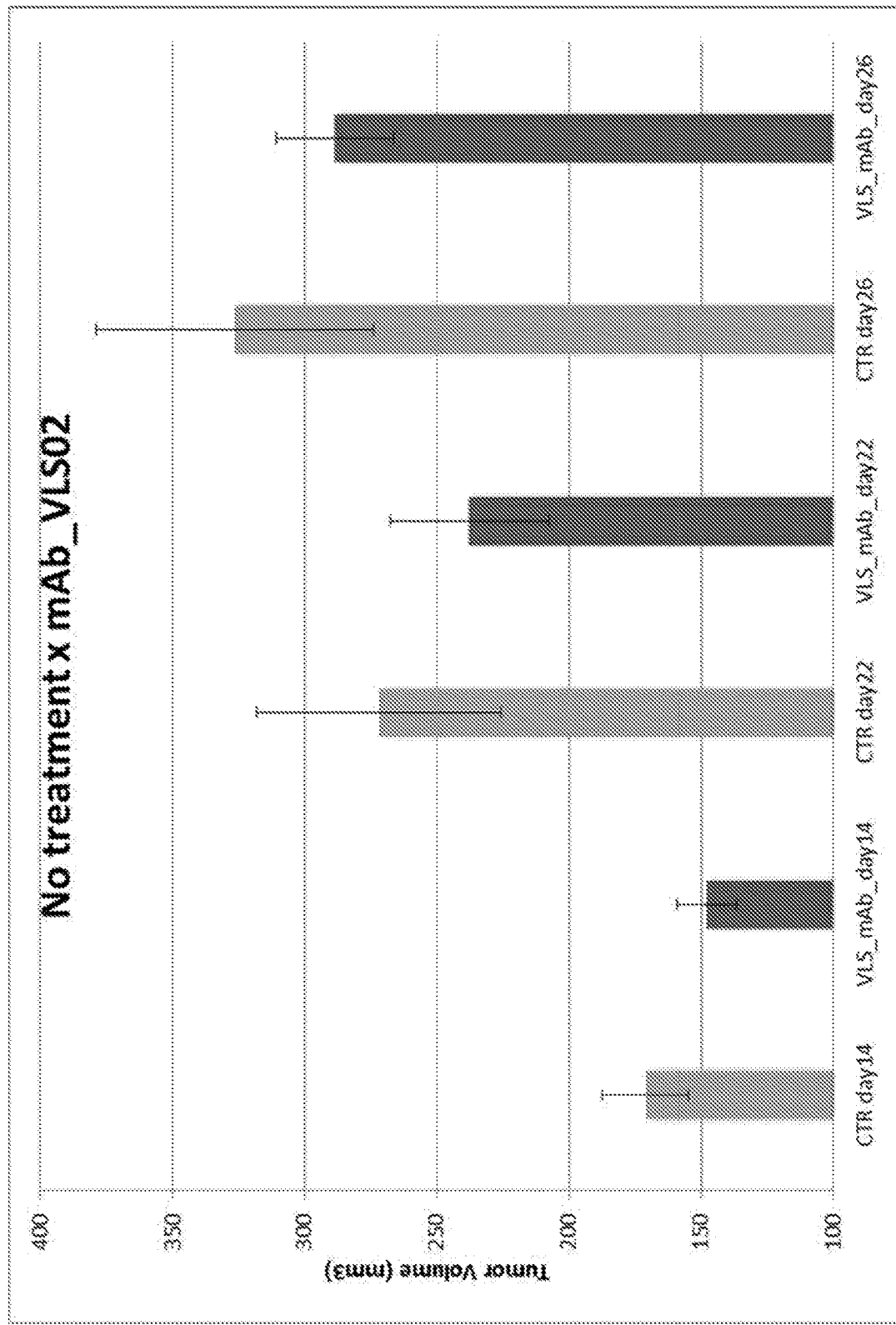
FIGS. 15A and 15B depict the effect of monoclonal antibody mAb_VLS02 as a single agent (FIG. 15A) and in combination with HERCEPTIN® (trastuzumab) (FIG. 15B) in reducing tumor volume at the last treatment point (day 14) and 8 and 12 days later. Reduced tumor size remained even at day 22 and day 26.
Figure 15:
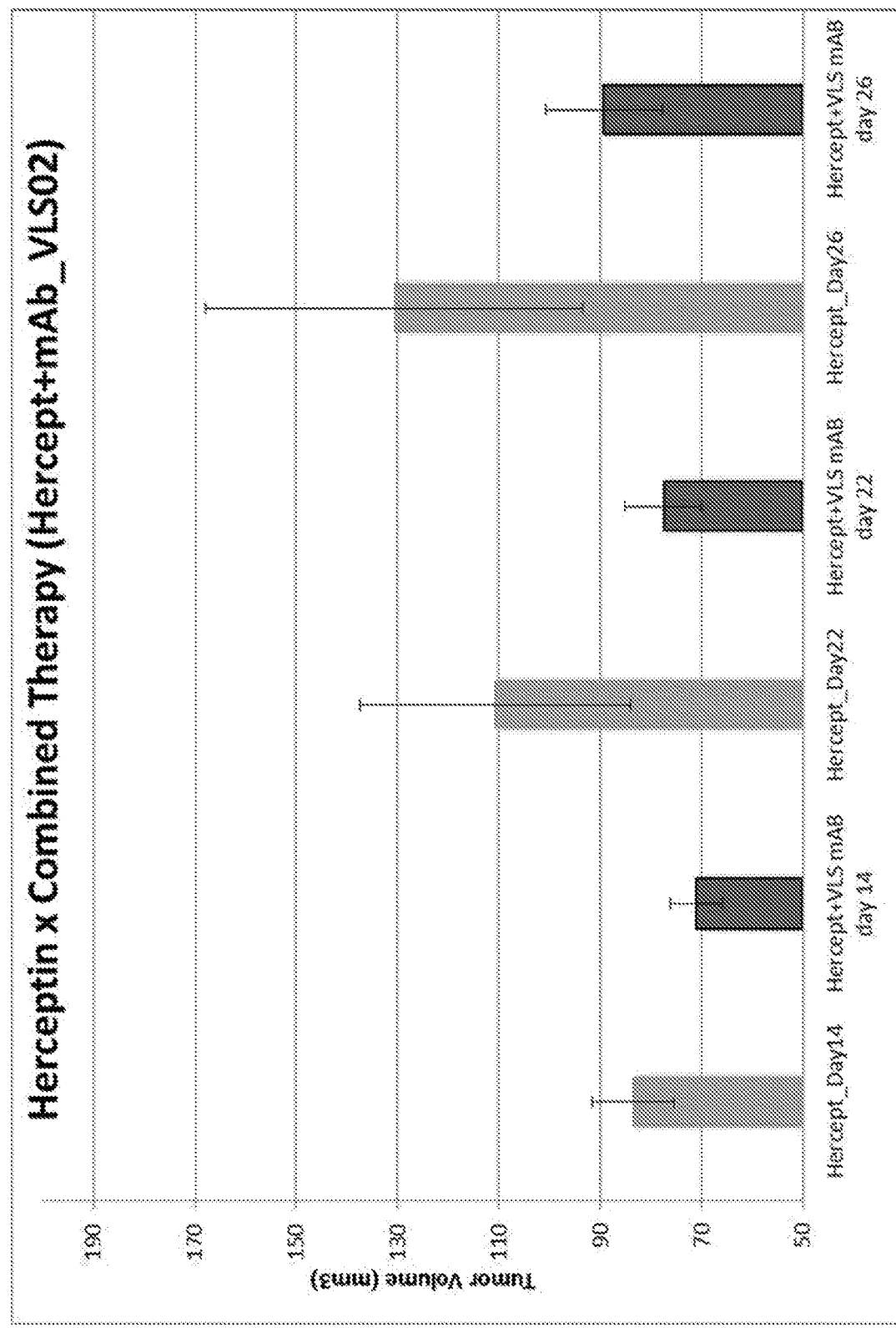
Figure 16:
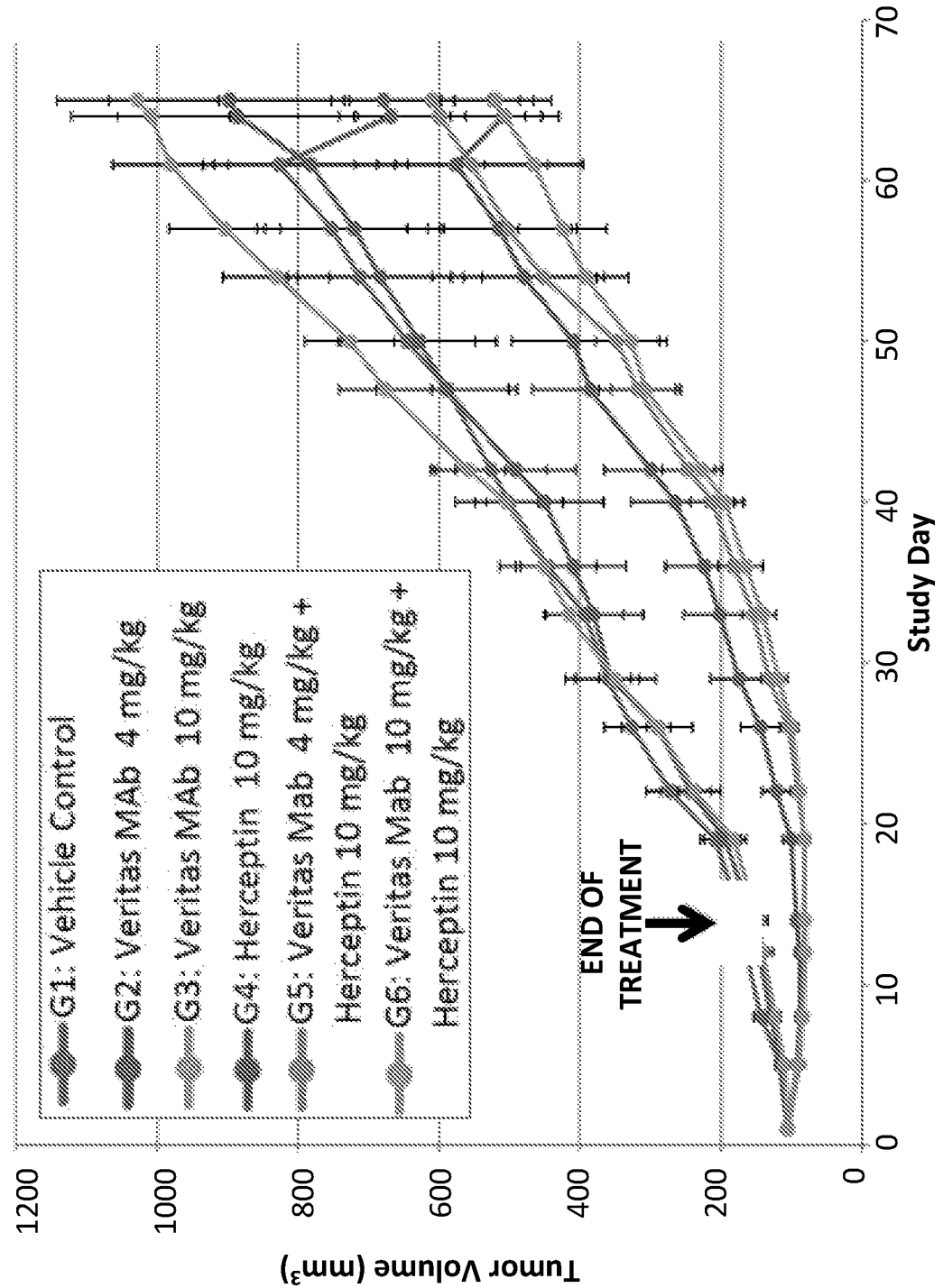
FIG. 16 depicts the efficacy of monoclonal antibody mAb_VLS02 alone and in combination with HERCEPTIN® (trastuzumab) in reducing tumor volume at the last treatment point (day 14) and fifteen days after (day 65).

The monoclonal antibody mAb_VLS02 of the present invention enhances the inhibitory effect of HERCEPTIN® (trastuzumab) on tumor growth in the N87 Human Gastric Tumor xenograft model (FIGS. 15 and 16).

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated or purified antibody or subsequence thereof that binds to a region of Cadherin-1 (CDH1) between the extracellular domain and the transmembrane domain, wherein the antibody or subsequence comprises a heavy chain variable region sequence and a light chain variable region sequence identical to a heavy chain variable region sequence and a light chain variable region sequence of an antibody produced by hybridoma cell line VLS-C1G (ATCC Accession No. PTA-124082).

2. The antibody or subsequence of claim 1, wherein the antibody or subsequence is produced by hybridoma cell line VLS-C1G (ATCC Accession No. PTA-124082).

3. The antibody or subsequence of claim 1, wherein the antibody or subsequence has the ability to inhibit CDH1 cleavage by matrix metallopeptidase 9 (MMP-9) and is humanized.

4. The antibody or subsequence of claim 1, wherein the antibody or subsequence comprises a single-chain variable fragment (scFv) comprising a heavy chain variable region and light chain variable region.

5. The antibody or subsequence of claim 4, wherein the scFv is part of a multivalent scFv.

6. The antibody or subsequence of claim 5, wherein the multivalent scFv is a diabody.

7. The antibody or subsequence of claim 1, wherein the antibody or subsequence is labeled with one or more labels selected from the group consisting of: a biotin label, a fluorescent label, an enzyme label, a coenzyme label, a chemiluminescent label, and a radioactive isotope label.

8. A pharmaceutical composition comprising the antibody or subsequence thereof of claim 1 and a pharmaceutically acceptable excipient or carrier.

9. The pharmaceutical composition of claim 8 further comprising an additional antibody or subsequence thereof that binds to a member of the epidermal growth factor receptor family.

10. The pharmaceutical composition of claim 9, wherein the member of the epidermal growth factor receptor family is HER2.

11. The pharmaceutical composition of claim 10, wherein the additional antibody is trastuzumab.

12. A method of reducing tumor growth or treating cancer in a mammal, comprising administering an effective amount of the antibody or subsequence of claim 1 to the mammal wherein the tumor or cancer is adenocarcinoma or of a gastric or ovarian origin.

13. The method of claim 12, wherein the mammal is a human.

14. The method of claim 12, further comprising administering a chemotherapeutic agent, a second antibody binding to a member of the epidermal growth factor receptor family, or both to the mammal.

15. The method of claim 14, wherein the member of the epidermal growth factor receptor family is HER2 and the second antibody is trastuzumab.

16. A method of reducing tumor growth or treating cancer in a mammal, comprising administering an effective amount of the antibody or subsequence of claim 1 to the mammal, the method further comprising diagnosing cancer by:
   obtaining a biological sample from a subject at risk of having a cancer and a control sample known to be negative for the cancer; and
   detecting the expression of intact CDH1, soluble CDH1, or both in the biological sample and the control sample with the antibody or subsequence of claim 1,
   wherein a reduced expression of intact CDH1, an increased expression of soluble CDH1, or both in the biological sample compared to the control sample indicates the presence of cancer in biological sample of the subject.

17. The method of claim 16, wherein the biological sample is selected from the group consisting of: blood, serum, plasma, saliva, and urine.

* * * * *

```
                       SEQUENCE LISTING

<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: linker segment

<400> SEQUENCE: 1

Val Glu Ala Gly Leu Gln Ile Pro Ala
1               5

<210> SEQ ID NO 2
<211> LENGTH: 14
<212> TYPE: PRT
<213> ORGANISM: Artificial Sequence
<220> FEATURE:
<223> OTHER INFORMATION: linker segment

<400> SEQUENCE: 2

Arg Lys Ala Gln Pro Val Glu Ala Gly Leu Gln Ile Pro Ala
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: synthetic peptide

<400> SEQUENCE: 3

Val Glu Ala Gly Leu Gln Ile Pro Ala Cys
1               5                   10

<210> SEQ ID NO 4
<211> LENGTH: 15
<212> TYPE: PRT
<213> ORGANISM: Artificial Sequence
<220> FEATURE:
<223> OTHER INFORMATION: synthetic peptide

<400> SEQUENCE: 4

Arg Lys Ala Gln Pro Val Glu Ala Gly Leu Gln Ile Pro Ala Cys
1               5                   10                  15

<210> SEQ ID NO 5
<211> LENGTH: 34
<212> TYPE: PRT
<213> ORGANISM: Artificial Sequence
<220> FEATURE:
<223> OTHER INFORMATION: linker segment

<400> SEQUENCE: 5

Lys Ala Gln Pro Val Glu Ala Gly Leu Gln Ile Pro Ala Ile Leu Gly
1               5                   10                  15

Ile Leu Gly Gly Ile Leu Ala Leu Leu Ile Leu Ile Leu Leu Leu Leu
            20                  25                  30

Leu Phe

<210> SEQ ID NO 6
<211> LENGTH: 29
<212> TYPE: PRT
<213> ORGANISM: Artificial Sequence
<220> FEATURE:
<223> OTHER INFORMATION: linker segment

<400> SEQUENCE: 6

Pro Gly Gln Glu Ala Gly Leu Gly Gln Val Pro Leu Ile Val Gly Ile
1               5                   10                  15

Leu Leu Val Leu Met Ala Val Val Leu Ala Ser Leu Ile
            20                  25

<210> SEQ ID NO 7
<211> LENGTH: 29
<212> TYPE: PRT
<213> ORGANISM: Artificial Sequence
<220> FEATURE:
<223> OTHER INFORMATION: linker segment

<400> SEQUENCE: 7

Thr Thr Ser Gly Pro Ile Arg Thr Pro Gln Ile Pro Glu Trp Leu Ile
1               5                   10                  15

Ile Leu Ala Ser Leu Leu Ala Leu Ala Leu Ile Leu Ala
            20                  25

<210> SEQ ID NO 8
<211> LENGTH: 31

```
<212> TYPE: PRT
<213> ORGANISM: Artificial Sequence
<220> FEATURE:
<223> OTHER INFORMATION: linker segment

<400> SEQUENCE: 8

Met Ala Ala Ser Leu Ser Pro Gly Ala Leu Ile Ala Leu Leu Val Cys
1               5                   10                  15
Val Leu Ile Leu Val Val Leu Val Leu Leu Ile Leu Thr Leu Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: linker segment

<400> SEQUENCE: 9

Pro Lys Ile Pro Ser Ile Ala Thr Gly Met Val Gly Ala Leu Leu Leu
1               5                   10                  15
Leu Leu Val Val Ala Leu Gly Ile Gly Leu Phe Met Arg Arg
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: linker segment

<400> SEQUENCE: 10

Pro Pro Glu Pro Ser Val Pro Leu Leu Pro Leu Leu Val Ala Gly Ala
1               5                   10                  15
Val Leu Leu Leu Val Ile Leu Val Leu Gly Val Met Val Ala Arg Arg
            20                  25                  30

<210> SEQ ID NO 11
<211> LENGTH: 23
<212> TYPE: PRT
<213> ORGANISM: Artificial Sequence
<220> FEATURE:
<223> OTHER INFORMATION: linker segment

<400> SEQUENCE: 11

Ser Ser Gln Pro Thr Ile Pro Ile Val Gly Ile Ile Ala Gly Leu Val
1               5                   10                  15
Leu Leu Gly Ala Val Ile Thr
            20

<210> SEQ ID NO 12
<211> LENGTH: 23
<212> TYPE: PRT
<213> ORGANISM: Artificial Sequence
<220> FEATURE:
<223> OTHER INFORMATION: linker segment

<400> SEQUENCE: 12

Pro Met Arg Trp Pro Phe Phe Leu Phe Ile Pro Phe Phe Ile Ile Phe
1               5                   10                  15
Cys Val Leu Ile Ala Ile Met
            20

<210> SEQ ID NO 13
```

```
<211> LENGTH: 26
<212> TYPE: PRT
<213> ORGANISM: Artificial Sequence
<220> FEATURE:
<223> OTHER INFORMATION: linker segment

<400> SEQUENCE: 13

Val Gln Asp Ser Ser Ser Val Pro Leu Pro Thr Phe Leu Val Ala Gly
1               5                   10                  15

Gly Ser Leu Ala Phe Gly Thr Leu Leu Cys
            20                  25

<210> SEQ ID NO 14
<211> LENGTH: 882
<212> TYPE: PRT
<213> ORGANISM: Homo sapiens

<400> SEQUENCE: 14

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300
```

```
Leu Ser Gln Asp Pro Glu Leu Pro Asp Lys Asn Met Phe Thr Ile Asn
305                 310                 315                 320

Arg Asn Thr Gly Val Ile Ser Val Thr Thr Gly Leu Asp Arg Glu
            325                 330                 335

Ser Phe Pro Thr Tyr Thr Leu Val Val Gln Ala Ala Asp Leu Gln Gly
                340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
            370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
            450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
            595                 600                 605

Pro Gln Val Ile Asn Ile Asp Ala Asp Leu Pro Pro Asn Thr Ser
610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
            690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
```

```
                    725                 730                 735
Val Lys Glu Pro Leu Leu Pro Pro Glu Asp Asp Thr Arg Asp Asn Val
                740                 745                 750

Tyr Tyr Tyr Asp Glu Glu Gly Gly Gly Glu Glu Asp Gln Asp Phe Asp
                755                 760                 765

Leu Ser Gln Leu His Arg Gly Leu Asp Ala Arg Pro Glu Val Thr Arg
            770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
                820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp

<210> SEQ ID NO 15
<211> LENGTH: 15
<212> TYPE: PRT
<213> ORGANISM: Artificial Sequence
<220> FEATURE:
<223> OTHER INFORMATION: linker segment

<400> SEQUENCE: 15

Arg Lys Ala Gln Pro Val Glu Ala Gly Leu Gln Ile Pro Ala Ile
1               5                   10                  15
```